(12) United States Patent
Nurok et al.

(10) Patent No.: US 7,736,517 B2
(45) Date of Patent: Jun. 15, 2010

(54) METHOD AND APPARATUS FOR PERFORMING PLANAR ELECTROCHROMATOGRAPHY AT ELEVATED PRESSURE

(75) Inventors: David Nurok, Indianapolis, IN (US); Robert E. Santini, West Lafayette, IN (US); Randall W. Replogle, Delphi, IN (US); Gregory L. Hawkins, Frankfort, IN (US); Henry L. Hawkins, legal representative, Frankfort, IN (US); James M. Koers, Indianapolis, IN (US)

(73) Assignees: Indiana University Research and Technology Corporation, Indianapolis, IN (US); Purdue Research Foundation, West Lafayette, IN (US)

( * ) Notice: Subject to any disclaimer, the term of this patent is extended or adjusted under 35 U.S.C. 154(b) by 1114 days.

(21) Appl. No.: 10/560,869

(22) PCT Filed: Jun. 17, 2004

(86) PCT No.: PCT/US2004/019438
§ 371 (c)(1), (2), (4) Date: Dec. 14, 2005

(87) PCT Pub. No.: WO2005/000443
PCT Pub. Date: Jan. 6, 2005

(65) Prior Publication Data
US 2006/0175259 A1     Aug. 10, 2006

Related U.S. Application Data

(60) Provisional application No. 60/537,763, filed on Jan. 20, 2004, provisional application No. 60/479,700, filed on Jun. 19, 2003.

(51) Int. Cl.
B01D 15/08 (2006.01)
C02F 1/28 (2006.01)
B01D 57/02 (2006.01)

(52) U.S. Cl. .................. 210/658; 210/656; 210/198.2; 204/554

(58) Field of Classification Search ............. 210/656, 210/658, 198.2; 72/453.06; 100/90; 204/554
See application file for complete search history.

(56) References Cited

U.S. PATENT DOCUMENTS 3,864,250 A    2/1975    Perry (Continued)

FOREIGN PATENT DOCUMENTS

WO        0051720        9/2000

(Continued)

OTHER PUBLICATIONS

*Conference Report*; Journal of Planar Chromatography, 1993; 355-356; Authored by Ian Davies.

(Continued)

*Primary Examiner* — Krishnan S Menon
*Assistant Examiner* — Katherine Zalasky
(74) *Attorney, Agent, or Firm* — Barnes & Thornburg LLP

(57) ABSTRACT

According to one aspect of the disclosure, there is provided an apparatus (210) for performing electrochromatography. The apparatus (210) includes a die block (222) which is movable to exert a pressure greater than atmospheric pressure on a chromatography sample plate during performance of an electrochromatography procedure. A method of performing electrochromatography is also disclosed.

10 Claims, 15 Drawing Sheets

U.S. PATENT DOCUMENTS

| | | | |
|---|---|---|---|
| 4,346,001 A | 8/1982 | Tyihák et al. | |
| 4,438,205 A | 3/1984 | Saint-Leger et al. | |
| 4,591,524 A | 5/1986 | Tyihák et al. | |
| 4,671,870 A | 6/1987 | Tompa et al. | |
| 4,671,871 A | 6/1987 | Székely et al. | |
| 4,708,782 A | 11/1987 | Andresen et al. | |
| 4,740,298 A | 4/1988 | Andresen et al. | |
| 4,865,729 A | 9/1989 | Saxena et al. | |
| 5,248,426 A | 9/1993 | Stillian et al. | |
| 5,350,510 A | 9/1994 | Partney, Jr. | |
| 6,303,029 B1 | 10/2001 | Nurok et al. | |
| 2003/0019816 A1* | 1/2003 | Mincsovics et al. | 210/741 |
| 2004/0020834 A1* | 2/2004 | Mincsovics et al. | 210/198.2 |
| 2004/0104173 A1* | 6/2004 | Manach et al. | 210/656 |

FOREIGN PATENT DOCUMENTS

WO      WO 01/50123 A1 * 7/2001

OTHER PUBLICATIONS

*Electroosmotically driven thin-layer electrochromatography on silica media*; 1999; J. Chromatogr. 844; 333-340; Authored by Howard et al.

*Evaporation-induced solvent migration in electrically-driven thin layer chromatography*; 1999, J. Chromatogr. 841; 127-132; Authored by Shafik et al.

*Electro-osmosis: A new concept for high-speed liquid chromatography*; Journal of Chromatography; 1974; 99; 23-30; Authored by Pretorius et al.

*Planar Electrochromatography on non-wetted thin-layers*; Chromatographia; Jan. 1994; vol. 38, No. ½; 83-87; Authored by Pukl et al.

*Planar Electrophoresis and Electrochromatography; Time to Revisit these Techniques?*; Journal of Planar Chromatography; Sep./Oct. 97; vol. 10; 332-335; Authored by Poole et al.

*Electrokinetic Ultrafiltration Analysis of Polysaccharides: A new Approach to the Chromatography of Large Molecules*; International Congress on Analytical Chemistry; Jun. 3, 1952; 964-969; Authored by D. L. Mould.

*Separations of Polysaccharides related to Starch by Electrokinetic Ultrafiltration in Collodin Membranes*; The Rowett Research Institute, Bucksburn, Aberdeenshire; Apr. 15, 1954; 571-585; Authored by D. L. Mould.

D. Nurok et al., "The Performance of Planar Chromatography using Electroosmotic Flow", *Journal of Planar Chromatography*, vol. 11, Jul./Aug. 1998, pp. 244-246.

D. Nurock et al., "Separation Using Planar Chromatography with Electroosmotic Flow", *Journal of Chromatography A*, 903, 2000, pp. 211-217.

D. Nurock et al., "Variables that Affect Performance in Planar Chromatography with Electroosmotic Flow", *Journal of Planar Chromatography*, vol. 14, Nov./Dec. 2001, pp. 409-414.

D. Nurock et al., "The Performance of Planar Electrochromatography in Horizontal Chamber", *Journal of Planar Chromatography*, vol. 15, Sep./Oct. 2002, pp. 320-323.

D. Nurock et al., "Role of Buffer Concentration and Applied Voltage in Obtaining a Good Separation in Planar Electrochromatography", *Journal of Chromatrography A*, 983, 2003, pp. 247-253.

T. H. Dzido et al., "Planar Electromatography in Horizontal Chamber with Cooling of the Chromatographic Plate", *Proc. International Symposium on Planar Separations*, Budapest, 2003, pp. 129-138.

T. Dzido et al., "Application of a Horizontal DS Chamber to Planar Electrochromatography", *Journal of Planar Chromatography*, vol. 16, May/Jun. 2003, pp. 176-182.

I. Malinowska et al., "Planar Electrochromatography on Silica and Alumina", *Journal of Planar Chromatography*, vol. 11, Nov./Dec. 1998, pp. 411-416.

I. Malinowska, The Inlfuence of Electric Fields on the Chromatographic Process in TLC, *Journal of Planar Chromatography*, vol. 12, Nov./Dec. 1999, pp. 408-415.

I. Malinowska, The Inlfuence of Electric Fields on the Chromatographic Process in TLC, *Journal of Planar Chromatography*, vol. 12, Nov./Dec. 1999, pp. 408-415.

I. Malinowska, "Some Aspects of the Effect of an Electric Field in Reversed-Phase Thin-Layer Chromatography", *ACTA Chromatographica*, No. 11, 2001, pp. 204-214.

I. Malinowska et al., "The Effect of Electric Fields on Solute Migration and Mixture Separation in TLC", *Journal of Planar Chromatography*, vol. 15, Nov./Dec. 2002, pp. 418-424.

V. Coman et al., "Planar Dielectrochromatogrphy—A Perspective Technique", *Journal of Planar Chromatography*, vol. 16, Sep./Oct. 2003, pp. 338-346.

S. Kreibik et al., "Horizontal Planar Dielectrochromatography. I. Preliminary Results", *Journal of Planar Chromatography*, vol. 15, Nov./Dec. 2002, pp. 425-428.

J. K. Róžlo et al., "10 Electroosmotically driven TLC—in Planar Chromatography: A Retrospective View for the Third Millennium, Nyiredy, SZ. ed.", *Springer Scientific*, Budapest, Hungry, 2001, pp. 200-219.

R. Consden et al., "Ionophoresis in Silica Jelly—A Method for the Separation of Amino-Acids and Peptides", *Biochem. J.*, vol. 40, 1946, pp. 33-41.

D. Nurock et al., "Apparatus and Initial Results for Pressurized Planar Electrochromatography", *Analytical Chemistry*, vol. 76, No. 6, Mar. 15, 2004, pp. 1690-1695.

J. M. Koers et al., "Performance of Planar Electrochromatography at Elevated Pressure", *Proc. International Symposium on Planar Separations*, Budapest, 2003, pp. 123-128.

D. Nurok, "Planar Electrochromatography", *Journal of Chromatography A*, vol. 1044, 2004, pp. 83-96.

T. H. Dzido et al., "Application of Horizontal Chamber for Separation in Opened and Closed Systems of Planar Electrochromatograpy", *Proc. International Symposium on Planar Separations*, Budapest, 2003, pp. 19-28.

PCT International Search Report for PCT Application No. PCT/US04/19438, Nov. 24, 2004, 6 pgs.

Nyiredy, S., "The bridge between TLC and HPLC: overpressured layer chromatography (OPLC)," Trac, Trends in Analytical Chemistry, Elsevier, Amsterdam, NL, vol. 20, No. 2, Feb. 1, 2001, pp. 91-101.

Flodberg, G. et al., "A device for high pressure thin layer chromatography," Journal of Planar Chromatography - Modern TLC, 1995 HU, vol. 8, No. 1, 1995, pp. 10-13.

European Search Report for European Patent Application No. 04755556.0 - 2204 / 1648582 - PCT/US2004019438, Jan. 15, 2010, 3 pgs.

* cited by examiner

METHOD AND APPARATUS FOR PERFORMING PLANAR ELECTROCHROMATOGRAPHY AT ELEVATED PRESSURE

CROSS REFERENCE TO RELATED APPLICATIONS

This application is a U.S. national counterpart application, filed under 35 U.S.C. §371, of international application Ser. No. PCT/US2004/019438 filed Jun. 17, 2004, which claims priority to U.S. Provisional Patent Application No. 60/479,700 entitled "Method and Apparatus for Performing Planar Electrochromatography at Elevated Pressure" which was filed on Jun. 19, 2003, and U.S. Provisional Patent Application Ser. No. 60/537,763, entitled "Method and Apparatus for Performing Planar Electrochromatography at Elevated Pressure" which was filed on Jan. 20, 2004. The entireties of the disclosures of which are hereby incorporated by reference.

CROSS REFERENCE

Cross reference is made to copending, commonly assigned U.S. patent application Ser. No. 09/941,205 which is a continuation of U.S. patent application Ser. No. 09/426,297, now U.S. Pat. No. 6,303,029, both of which are hereby incorporated by reference.

TECHNICAL FIELD OF THE DISCLOSURE

The present disclosure relates generally to chromatography, and more particularly to planar electrochromatography at elevated pressure.

BACKGROUND OF THE DISCLOSURE

Numerous chromatography techniques have been developed which enable the separation of mixtures into individual chemical components. Electrochromatography is one such technique. Electrochromatography involves the use of an electrical potential applied across the sorbent layer. As described in commonly owned U.S. Pat. No. 6,303,029, desirable results may be achieved by performing electrochromatography at pressures greater than atmospheric pressure. Such a technique is referred to as Planar Electrochromatography at Elevated Pressure (PPEC). Planar Electrochromatography at Elevated Pressure builds on the notion that applying pressure to the layer prevents accumulation of liquid on the surface of the layer, and also allows the removal of heat from the system. This allows the use of higher voltages, which results in higher electric fields. This causes the mobile phase to migrate more rapidly, which shortens analysis time. High pressure also decreases the space between particles in the sorbent bed, and this increases the efficiency of the system.

SUMMARY OF THE DISCLOSURE

According to one aspect of the disclosure, there is provided an apparatus for performing electrochromatography. The apparatus includes a die block which is movable to exert a pressure greater than atmospheric pressure on a chromatography sample plate during performance of an electrochromatography procedure.

The sample plate may be sandwiched between the movable die block and another die block. The other die block may be stationary or may be movable.

The sample plate may be positioned in a plate holder. In certain illustrative embodiments, the plate holder includes a pair of frame members between which the sample plate is sandwiched. A thin cover slip may be positioned between the sample plate and the compression surface into which the plate is urged. A sheet of electrically insulating, thermally conducting material may be sandwiched between the plate and the compression surface into which the plate is urged.

The movable plate may be moved by use of a fluid ram. In certain implementations, the fluid ram is embodied as a hydraulic fluid ram.

According to another aspect of the present disclosure, there is provided a method of performing electrochromatography. The method includes the step of urging a die block toward a stationary phase supported on a sample plate so as to exert a pressure which is greater than atmospheric pressure against the stationary phase. An electrical potential is created across the stationary phase with a first electrode and a second electrode so as to cause a liquid mobile phase to be advanced across the stationary phase.

The sample plate may be sandwiched between the movable die block and another die block. The other die block may be stationary or may be movable.

The sample plate may be positioned in a plate holder. In certain illustrative embodiments, the plate holder includes a pair of frame members between which the sample plate is sandwiched. A thin cover slip may be positioned between the sample plate and the compression surface into which the plate is urged. A sheet of electrically insulating, thermally conducting material may be sandwiched between the plate and the compression surface into which the plate is urged.

The die block may be urged by use of a fluid ram. In certain implementations, the fluid ram is a hydraulic ram.

BRIEF DESCRIPTION OF THE DRAWINGS

The detailed description particularly refers to the accompanying figures in which.

DETAILED DESCRIPTION OF THE DISCLOSURE

Figure 1:
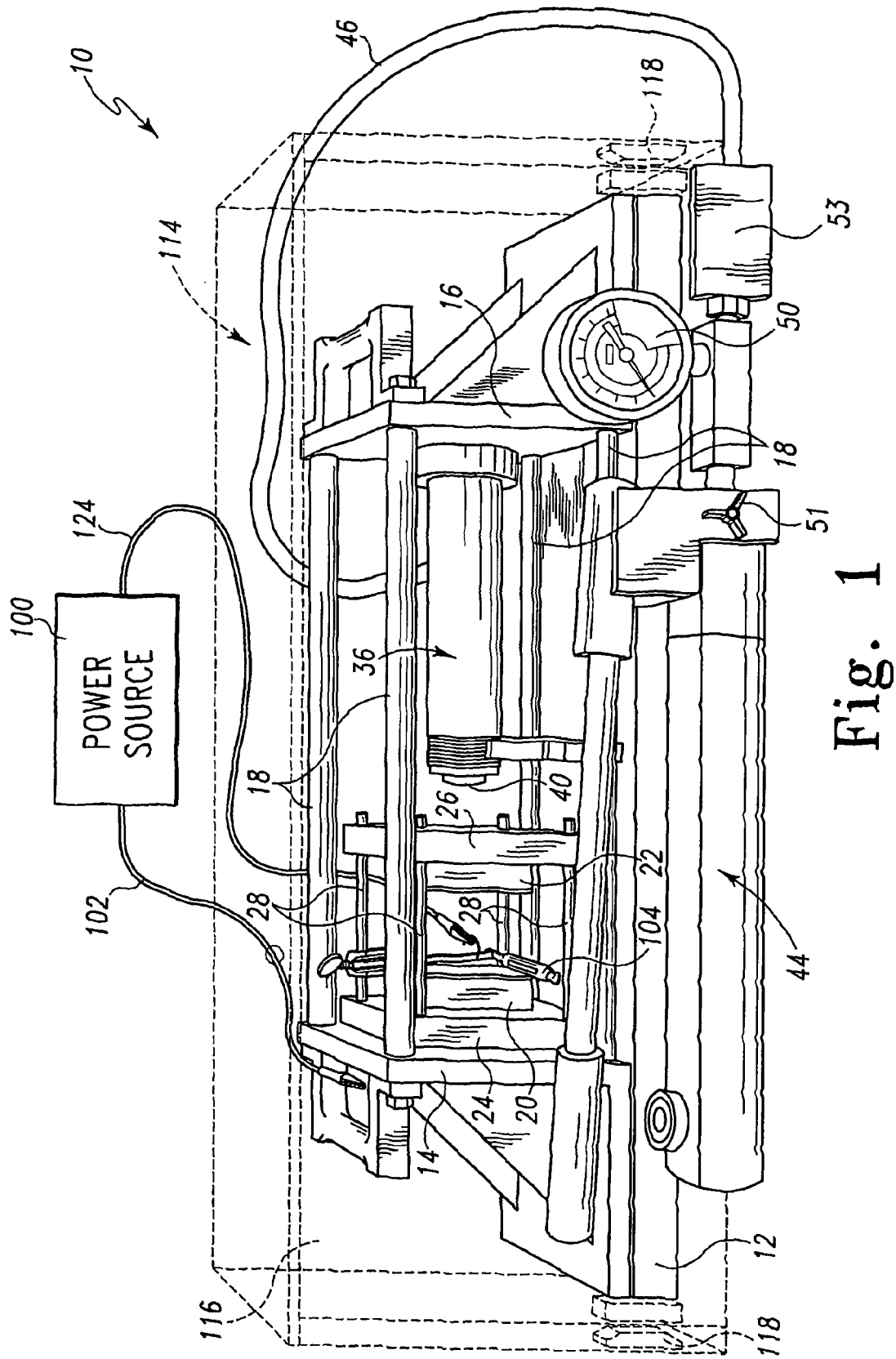
FIG. 1 is a perspective view of a chromatography apparatus for performing a planar electrochromatography at elevated pressure (PPEC) procedure.

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

Figure 2:
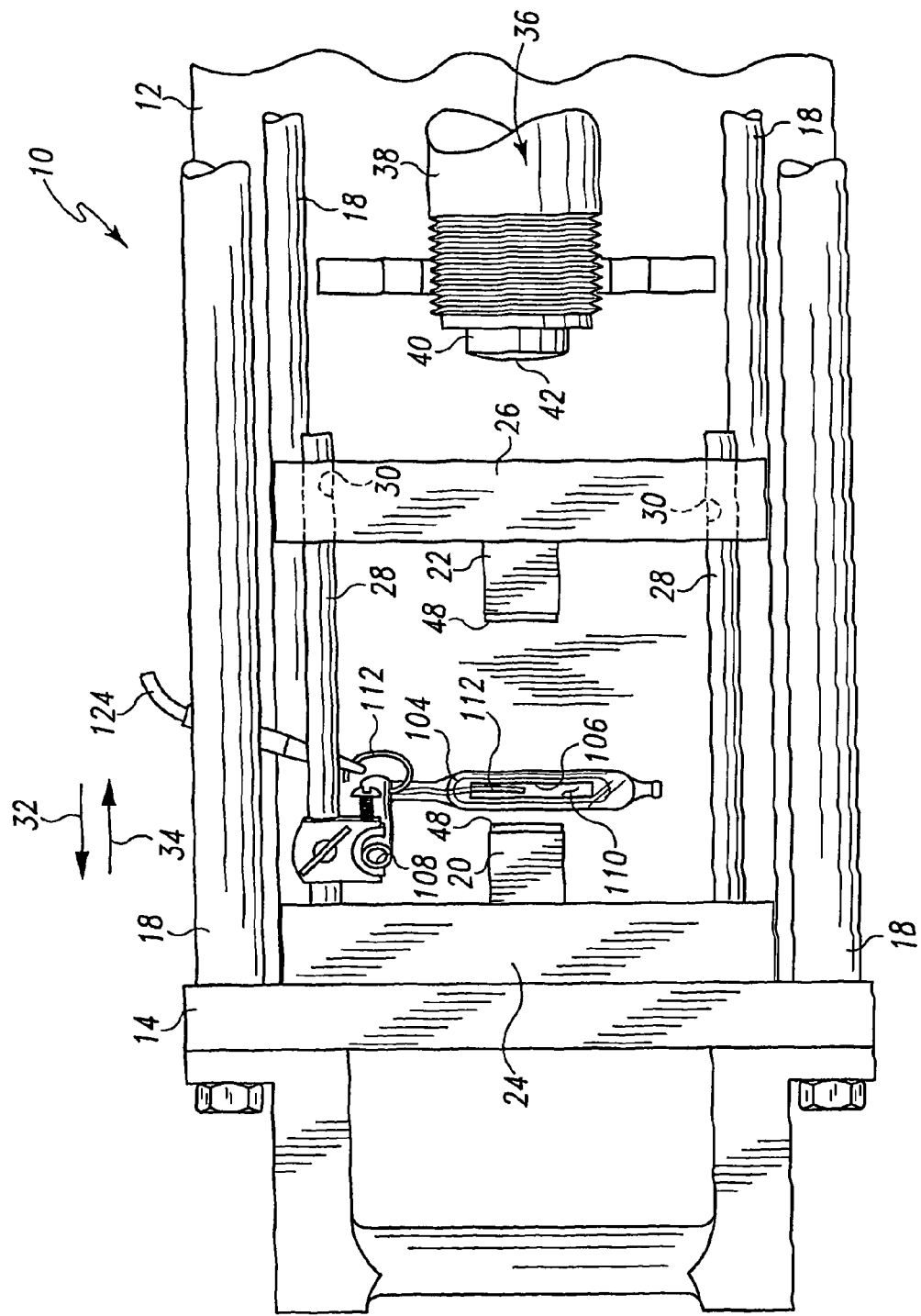
FIG. 2 is an enlarged fragmentary plan view of the chromatography apparatus of FIG. 1.
Figure 3:
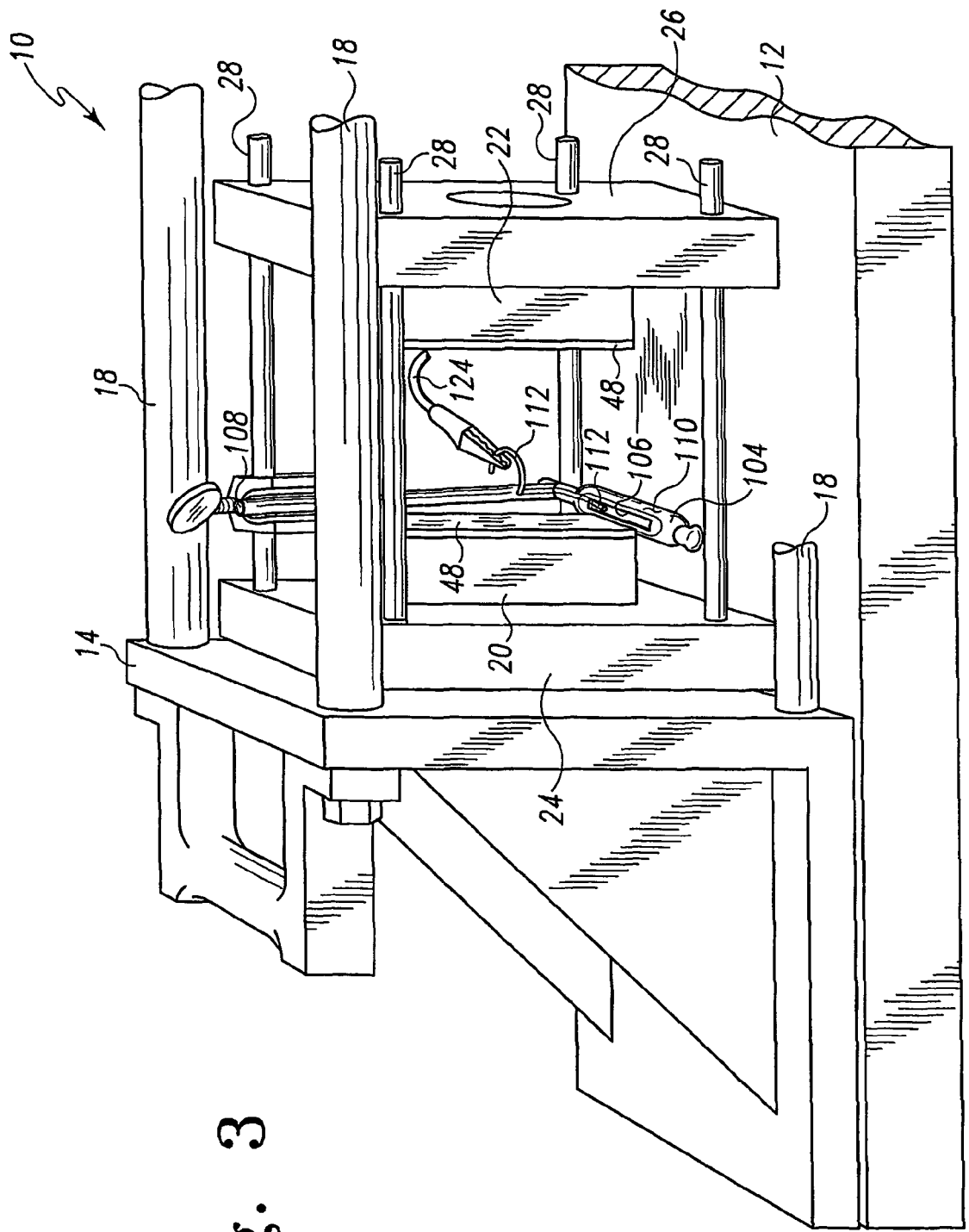
FIG. 3 is an enlarged fragmentary view of the chromatography apparatus of FIG. 1.

Referring now to FIGS. 1-3, there is shown a chromatography apparatus 10. The chromatography apparatus 10 includes a 1½"-thick lower plate 12 having a pair of upwardly extending support plates 14, 16 secured thereto. A number of struts 18 are secured to each of the support plates 14, 16. As shown in FIG. 1, the chromatography apparatus 10 also includes a pair of die blocks 20, 22. In the exemplary embodiment described herein, each of the die blocks 20, 22 has a width of 2.5 cm and is formed from metal, but may be formed from another material in other embodiments. The die block 20 is secured to a stationary plate 24. The plate 24 is secured to the support plate 14.

The die block 22 is secured to a movable plate 26. The die block 22 is movable relative to the die block 20. In particular, the stationary plate 24 has a number of rods 28 extending therefrom. The movable plate 26 has a corresponding number of holes 30 defined therein into which the rods 28 are received. As such, the movable plate 26, and hence the die block 22, may slide back and forth along the rods 28 in a direction toward the die block 20 (as indicated by the arrow 32 of FIG. 2) and in a direction away from the die block 20 (as indicated by the arrow 34 of FIG. 2).

Either one or both of the die blocks 20, 22 may be configured with a number of passages or other types of fluid lines (not shown). Such passages or other types of fluid lines may be defined in the die blocks 20, 22. Alternatively, such passages or other types of fluid lines may be embodied as separate structures positioned in contact with the die blocks 20, 22. A fluid such as a coolant may be advanced through such passages to cool the die blocks 20, 22 thereby enhancing the die blocks 20, 22 heat sink capabilities. In addition to, or in lieu of, the die blocks 20, 22, the plates 24, 26 may also have such passages or other types of fluid lines. Use of a fluid (e.g., a coolant) allows a sample plate to be maintained at a desired temperature including room temperature (or temperatures above or below room temperature) during a procedure. As such, the fluid may be used to cool a sample plate or maintain the plate at a desired constant temperature. Moreover, the aforedescribed arrangement of fluid passages/lines in the die blocks and/or plates may be utilized to create a temperature gradient along the sample plate's axis of mobile phase travel. Typically, the direction of electroosmotic flow would be toward the colder part of the gradient. It has been suggested that the formation of such a temperature gradient may generate sharpened peaks during sample analysis (which will lead to enhanced peak resolution). It should be appreciated that the aforedescribed arrangement of fluid passages/lines in the die blocks 20, 22 and/or the plates 24, 26 may be utilized to circulate a heated fluid so as to heat the sample plate, if desired.

As shown in FIG. 2, a thermally conducting, electrically insulating sheet 48 is positioned on the face of the die blocks 20, 22. The sheet 48 is a thermal conductor thereby allowing heat on a sample plate to be transferred to the die blocks 20, 22. The sheet 48 is also an electrical insulator thereby electrically insulating the sample plate from the die blocks 20, 22. The sheet 48 may be constructed with a variety of materials having such characteristics. One material which may be utilized in the construction of the sheet 48 is a thin sheet of aluminum nitride ceramic. In the exemplary embodiment described herein, the sheet 48 is attached to the face of the die blocks 20, 22 with drops of mineral oil. A piece of polymeric material such as Delrin®, which is commercially available from E.I. du Pont de Nemours and Company of Wilmington, Del., or other material (not shown) may be installed on the bottom surface of the die blocks 20, 22 in a manner which forms a lip on which the bottom of the sheet 48 rests. Such a lip facilitates maintenance of the sheet 48 in a desired location on the face of the die blocks 20, 22.

A fluid ram 36 is utilized to urge the movable plate 26 (and hence the die block 22) in the general direction of the arrow 32 (i.e., toward the stationary die block 20). Specifically, the fluid ram 36 includes a cylinder housing 38 having a rod 40 extending therefrom. During extension of the rod 40, a rod end 42 of the rod 40 is urged into contact with the side of the movable plate 26 opposite to the die block 22 thereby urging the plate 26 (and hence the die block 22) in the general direction of the arrow 32 of FIG. 2 (i.e., in a direction toward the stationary die block 20). In the exemplary embodiment described herein, the fluid ram 36 is embodied as a hydraulic ram, although other types of rams are contemplated. For example, the fluid ram may be embodied as a pneumatic ram.

Fluid pressure (e.g., hydraulic pressure) is generated by use of a manual fluid pump 44. Specifically, operation of the manual fluid pump 44 generates fluid pressure within a fluid line 46. The fluid line 46 is coupled to an inlet of the fluid ram 36. As such, fluid pressure generated by the manual fluid pump 44 is exerted on the head end (not shown) of the rod 40. A pressure gauge 50 outputs the magnitude of the fluid pressure within the fluid line 46 to a user. A pressure relief valve 51 may be used to reduce the fluid pressure in the fluid line 46. A shut-off valve 53 is positioned between the pressure gauge 50 and the end of the fluid line 46. The shut-off valve 53 maintains fluid pressure in the fluid system once a desired pressure has been obtained. In other words, the shut-off valve 53 prevents pressure down-drift in the fluid system. It should be appreciated that the shut-off valve 53 may not be used in certain designs of the chromatography apparatus 10.

Figure 4:
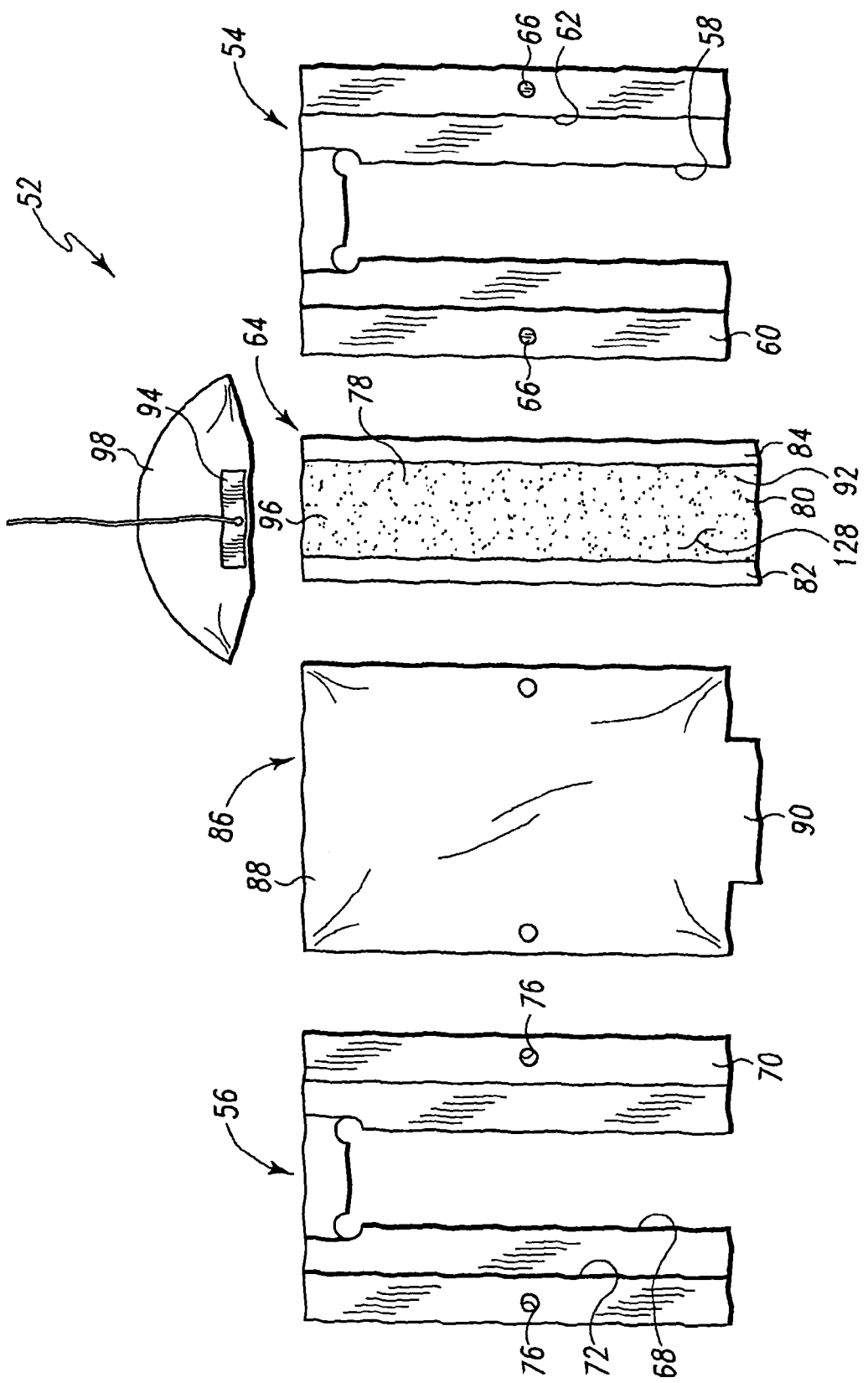
FIG. 4 is an exploded plan view of the plate holder of the chromatography apparatus of FIG. 1, note that a chromatography sample plate for use with the chromatography apparatus of FIG. 1 is also shown.
Figure 5:
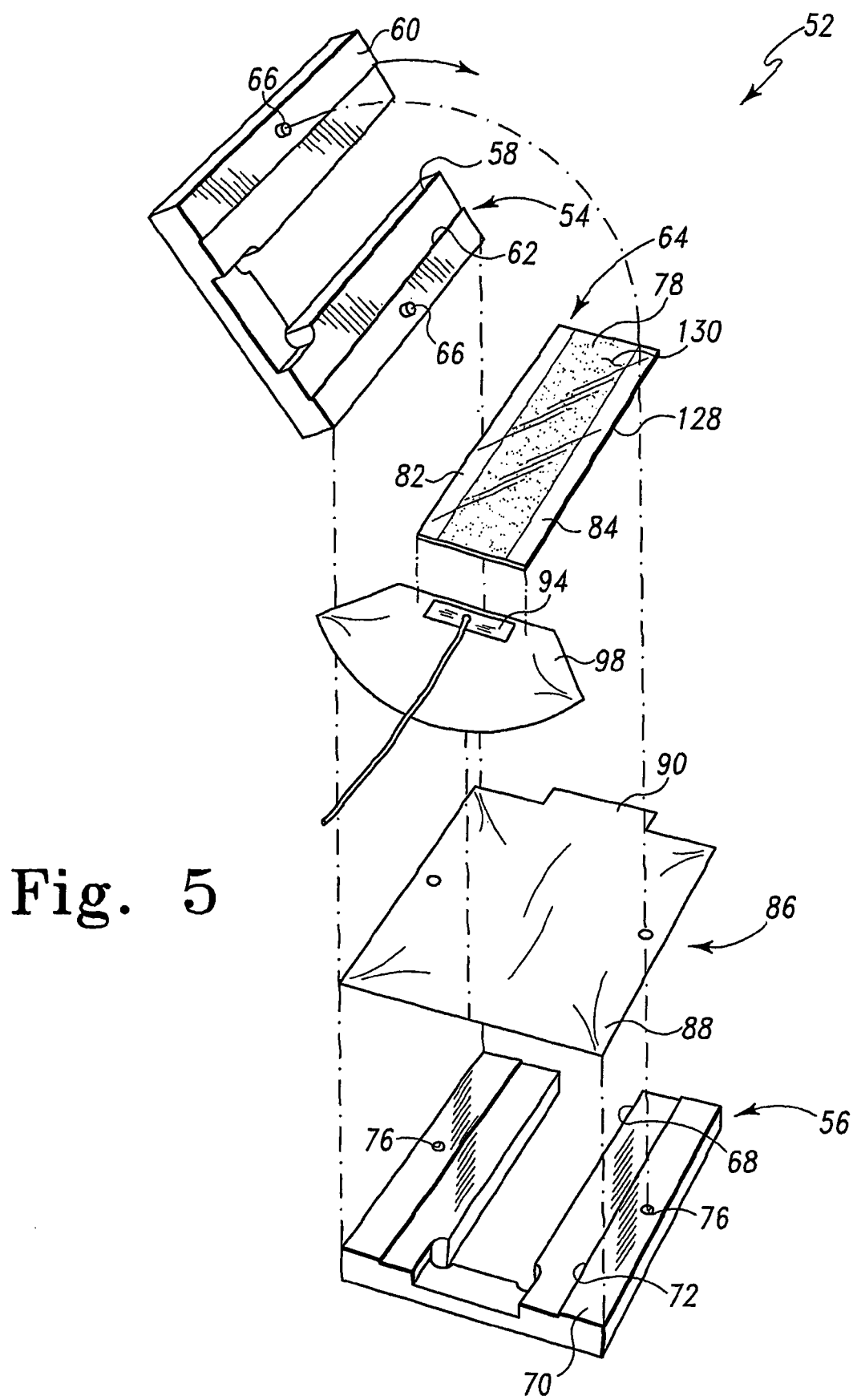
FIG. 5 is an exploded perspective view showing the order of assembly of the components of FIG. 4.
Figure 6:
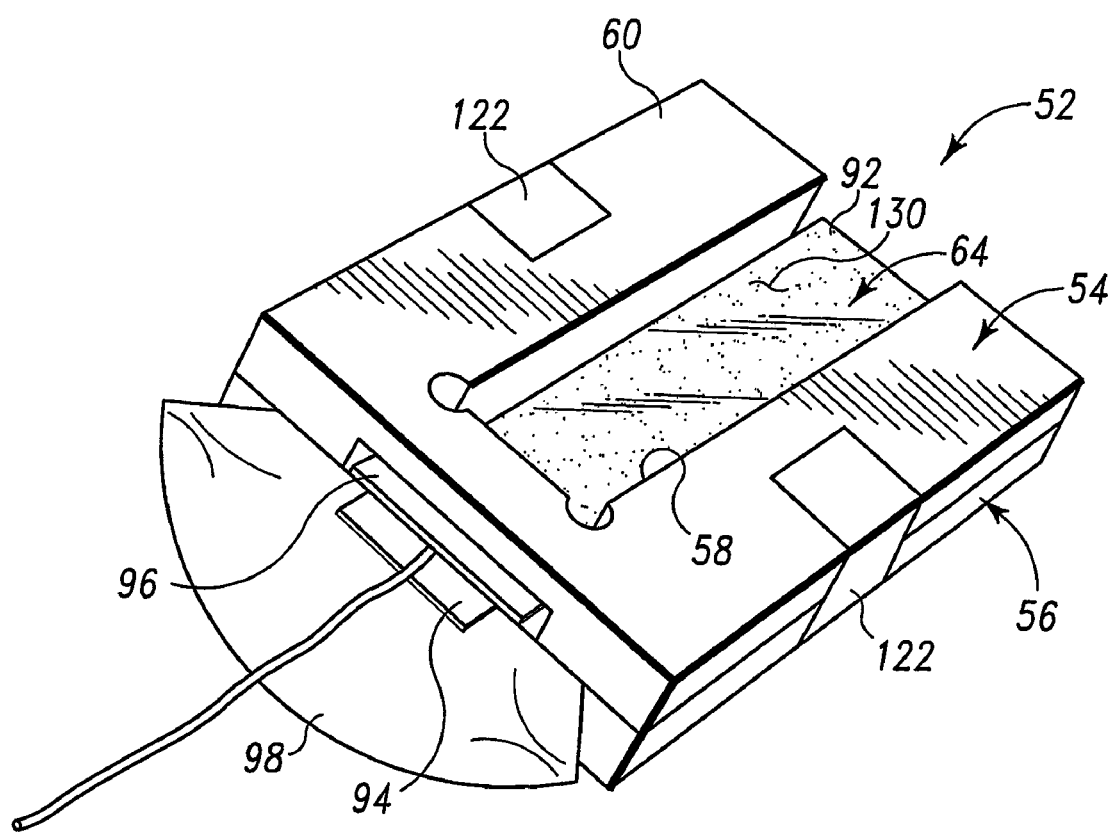
FIG. 6 is an enlarged perspective view showing the chromatography sample plate assembled in the plate holder.

As shown in FIGS. 4-6, the chromatography apparatus 10 also includes a plate holder 52. The plate holder includes a pair of frame members 54, 56. The frame members 54, 56 may be constructed with any type of electrically insulating material that is resistant to the solvents used in an electrochromatography procedure. In the exemplary embodiment described herein, the frame members 54, 56 are constructed with a polymeric material. One such polymeric material is Delrin®, which is commercially available from E.I. du Pont de Nemours and Company of Wilmington, Del.

The frame member 54 is substantially U-shaped with an opening 58 defined in a body 60 thereof. The body 60 also has a recess 62 defined therein. The recess 62 is positioned around the periphery of the opening 58. As will be discussed herein in greater detail, a chromatography sample plate 64 is positioned in the recess 62. The frame member 54 also includes a number of posts 66 extending outwardly from the body 60. As will be discussed herein in greater detail, the posts 66 are received into a corresponding number of alignment holes defined in the frame member 56 during assembly of the plate holder 52.

Similar to the frame member 54, the frame member 56 is substantially U-shaped with an opening 68 defined in a body 70 thereof. The body 70 also has a recess 72 defined therein. The recess 72 is positioned around the periphery of the opening 68. The chromatography sample plate 64 is positioned in the recess 72 during assembly of the plate holder 52. The recesses 62, 72 of the frame members 54, 56, respectively, may have the same depth, or, may be configured to have slightly different depths depending on the particular design of the plate holder 52. The frame member 56 also includes a number of alignment holes 76 defined in the body 60 thereof. The posts 66 of the frame member 54 are received into the alignment holes 76 of the frame member 56 during assembly of the plate holder 52.

The chromatography sample plate 64 includes a support substrate 78 such as a glass or plastic plate. The sample plate 64 also includes a chromatographic bed 80 (also referred to herein as a "stationary phase") disposed and adhered onto a front side 128 of the support substrate 78. An exemplary stationary phase 80 includes silica particles with bonded $C_{18}$ groups attached. In an exemplary implementation, the particle size of the silica may be in the range of about 2 micrometers to about 20 micrometers, although particles of smaller size (e.g., <1 micrometer) are certainly within the contemplated scope of the disclosure. Moreover, the thickness of the stationary phase 80 disposed on the surface of the substrate 78 may be in the range of about 5 microns to about 3 millimeters. It should be appreciated, however, that the thickness of the stationary phase 80 may be varied within, or even outside of, such a range to fit the needs of a given system design or experiment. One exemplary sample plate 64 is a catalog number 15389 (RP-18 $F_{254s}$ plate—which is made of up of a chemically modified silica) which is commercially available from Merck of Darmstadt, Germany. The sample plate 64 may also be embodied as any one of a number of TLC plates such as a LiChrospher $C_{18}$ plate which is also commercially available from Merck. Such a sample plate may include a bed of particles with or without a binder, where the particles may include the types used for packing an HPLC column. The stationary phase may also be embodied as a monolith.

The sample plate 64 may be one that has a sorbent layer prepared with a gradient in the concentration of the attached ligand groups. The concentration of ligand groups will increase in the direction of mobile phase flow. An example of a ligand is the octadecylsilyl group. The gradient will result in peak sharpening and better resolution if the electroosmotic flow is in the direction of increasing ligand concentration. The reason is that the leading edge of each spot will be moving more slowly (due to greater retention on the layer) than the trailing edge.

As shown in FIG. 4, the side edge portions 82, 84 of the sample plate 64 are devoid of stationary phase 80. The sample plate 64 may be manufactured in such a configuration, or the edge portions 82, 84 may be scraped to remove the stationary phase therefrom. In either case, the support substrate 78 is exposed along the edge portions 82, 84. As will be described herein in greater detail, such a configuration allows for the sealing of the stationary phase 80 thereby preventing the mobile phase from flowing beyond the edges of the stationary phase 80. To facilitate such sealing of the mobile phase, a sealant may be applied to the side edge portions 82, 84. The sealant may be applied in a manner which extends a short distance into the stationary phase (i.e., extends into the stationary phase 80 beyond the inner edges of the edge portions 82, 84), if desired. Numerous types of sealants may be used. Two exemplary commercially available sealants include polymer beads (an ethylene/vinyl acetate copolymer having a vinyl acetate content of 45%) which is available as catalog number 24937-78-8 from Aldrich Chemical Company of Milwaukee, Wis., along with a Fast Set Epoxy (a two part resin and hardener) which is commercially available from Ross Products of Columbus, Ohio. Another exemplary commercially available sealant is President Vinylpolysiloxane (a two part resin and hardener) which is commercially available from Coltene A.G. of Alstatten, Switzerland. It should be appreciated that in certain configurations, adequate sealing of the stationary phase 80 may be achieved without the use of a sealant.

The plate holder 52 also includes a thin cover slip 86. The cover slip 86 may be constructed of any type of material. In the exemplary embodiment described herein, the cover slip 86 is constructed with 0.01" thick Teflon. The cover slip 86 is positioned over the front side 128 of the sample plate 64 (i.e., the side having the stationary phase 80 disposed thereon) during assembly of the plate holder 52. In such a way, the cover slip 86 facilitates maintenance of the liquid phase within the stationary phase 80 during advancement of the liquid phase therethrough.

The cover slip 86 includes a main body 88 having a extension section 90 extending from a lower edge thereof. The extension section 90 is configured to cover a lower portion 92 of the sample plate 64. In particular, as will herein be described in greater detail, when the sample plate 64 is positioned in the plate holder 52, the lower portion 92 of the sample plate 64 extends beyond the bottom edges of the plate holder 52. The lower portion 92 is positioned in a reservoir of mobile phase during performance of a chromatographic procedure. By use of a cover slip having the extension section 90, liquid (i.e., mobile phase) is maintained between the front side 128 of the sample plate 64 (i.e., the side having the stationary phase disposed thereon) and the extension section 90.

As shown in FIGS. 5 and 6, an electrode 94 (in the exemplary embodiment described herein, the cathode) is in contact with an upper portion 96 of the sample plate 64 when the plate is positioned in the plate holder 52. Specifically, during assembly of the plate holder 52, the electrode 94 is sandwiched between the upper portion 96 of the front side 128 of the sample plate 64 (i.e., the side having the stationary phase 80 disposed thereon) and the frame member 56. Note that the frame members 54, 56 are configured such that the cathode 94 is not subjected to the pressures generated by the die blocks 20, 22. As such, a spacer (not shown), which may be compressible, may be inserted into the plate holder 52 to exert a slight compressive load on the cathode 94 to hold the cathode 94 in a desired position. The cathode 94 is electrically coupled to the stationary phase 80 of the sample plate 64, along with the mobile phase advancing therethrough. A wick 98 is also sandwiched between the upper portion 96 of the front side 128 of the sample plate 64 and the frame member 56. The wick 98 facilitates removal of the mobile phase which has reached the upper portion 96 of the sample plate 64 by allowing such mobile phase to migrate up the wick. In the exemplary embodiment described herein, the wick 98 is embodied as a piece of filter paper or any other suitable absorbent or wicking material. Other techniques or devices for removing the mobile phase may also be used.

In the exemplary embodiment described herein, the cathode 94 is embodied as a sheet of platinum foil (0.2 mm thick) having a stainless steel or platinum wire extending therefrom. The cathode 94 is electrically coupled to a power source 100 (see FIG. 1) via a power line 102 which is clipped, soldered, or otherwise secured to the end of the cathode's wire.

As shown in FIGS. 1 and 2, the chromatography apparatus 10 also includes a fluid reservoir 104. The fluid reservoir 104 includes an access opening 106 into which the lower portion 92 of the sample plate 64 (along with the extension section 90 of the cover slip 86) extends when the plate holder 52 is positioned in its test position. A fluid 110 (e.g., mobile phase) is advanced through the access opening 106 to fill the reservoir 104 to a desired fluid level. As shown in FIG. 3, an electrode 112 (in the exemplary embodiment described herein, the anode) extends through a hole in a wall of the reservoir 104 and into the liquid phase 110 accumulated therein. In the exemplary embodiment described herein, the anode 112 is embodied as a stainless steel or platinum wire which is electrically coupled to the power source 100 via a power line 124 clipped, soldered, or otherwise secured thereto.

One exemplary mobile phase 110 is 55% aqueous acetonitrile containing 50 mM acetate buffer. The concentration of this buffer, after adding the acetonitrile, is 25 mM in acetic acid and 25 mM in sodium acetate. The pH of the buffer is 4.7 before adding the acetonitrile. The components of such a mobile phase are commercially available. It should be appreciated that, as described in the above-incorporated patent (i.e., U.S. Pat. No. 6,303,029), the sample plate 64 may be pre-wetted with mobile phase 110 or an aqueous solution having a buffer concentration that matches that of the mobile phase 110. The dipping solution may also be a mobile phase that does not match the latter buffer concentration. One exemplary pre-wetting technique includes applying mobile phase (or other solution) to both the portion of the plate 64 located above the deposited sample spot(s) and the portion of the plate 64 located below the deposited sample spot(s), with the portion of the sample plate 64 on which the sample spot(s) is(are) located remaining dry. In such a technique, the same mobile phase may be applied to each portion of the plate 64, or, alternatively, a different mobile phase maybe applied to each portion (e.g., mobile phases having the same components at different concentrations or even different components). Alternatively, the plate 64 may be pre-wetted by dipping, spraying, or soaking the entire plate 64 in a solution (e.g. mobile phase). In such a case, the solution may be allowed to drain for a brief period of time (e.g., 15 seconds) in the direction of the long axis of the plate. Spraying may be substituted for dipping in the above procedures.

By placement of the cathode 94 in electrical contact with the upper portion 96 of the sample plate 64, and the anode 112 in electrical contact with the lower end portion 92 of the sample plate 64, an electrical potential is created between the cathode 94 and the anode 112 when the power source 100 is actuated. In the exemplary embodiment described herein, the electrical potential generated by the power source 100 is in the range of 500V-10,000V, although potentials outside of this range are also contemplated.

When an electrical potential is generated between the cathode 94 and the anode 112 electroosmotic flow occurs. Electroosmotic flow is explained as follows. The particles in the sorbent bed have a high concentration of surface silanol groups, and a large number of these are ionized at the pH used in PPEC. This causes the particles to have a negative charge, and this results in a high concentration of positive ions in the solution adjacent to the particles. These positive ions migrate towards the cathode 94 when an electric field is applied. This results in the bulk flow of liquid towards the cathode 94.

As discussed in the above-incorporated patent (i.e., U.S. Pat. No. 6,303,029), as the mobile phase 110 is advanced toward the cathode 94, the components of the sample spot deposited on the sample plate 64 partition between the mobile phase 110 and the stationary phase 80 based upon their differing physical and chemical characteristics. Since the components of the sample spot deposited on the sample plate 64 typically differ based upon, amongst other things, their polarity, charge, and size, the components are separated from one another as the sample plate 64 is developed.

Any stationary phase that is used in conventional TLC can be used in PPEC. The stationary phase for PPEC can also be a monolith. It can also consist of a bed of particles with or without a binder, where the particles may include the types used for packing an HPLC column.

Once the sample spot is separated into its individual components, the resultant separated spots may be detected or visualized using known techniques. For example, subsequent to development and drying, the separated spots may be visualized by using a scanning or video densitometer. In addition to such an "off-line" technique, it should be appreciated that the separated spots may be detected "on-line." In particular, the mobile phase 110 may be advanced from the sample plate 64 directly to a detector. In such a case, multiple detectors may be used to accommodate multiple sample spots. Such on-line analysis is particularly well suited for when a single sample is applied as a line across the sample plate 64 (as opposed to a series of spots). In such an application, a single detector could be used. This is useful for preparative separations. It can also be used for samples that contaminate the sample plate 64 since the sample plate is relatively inexpensive and may therefore be discarded.

The chromatography apparatus 10 also includes an enclosure or housing 114. The housing 114 surrounds the sample during performance of a chromatographic procedure. The housing 114 is generally constructed with a clear plastic material such as Plexiglas. The housing 114 includes an access door 116 having a number of switches 118 associated therewith which are used to deactivate the power source 100 and dissipate any charge stored by the apparatus if the door 116 is opened. The housing 114 has a hole (not shown) defined therein through which the fluid line 46 from the hand pump 44 to the fluid ram 36 extends.

To perform a electrochromatography procedure, the sample plate 64 is first wetted and then installed into the plate holder 52. To do so, as shown in FIG. 5, the frame member 56 may be positioned on a flat surface with the surface of the frame member's body 70 having the holes 76 defined therein facing upwardly. The cover slip 86 is then positioned on the upwardly facing surface of the frame member 56. Note that the main body 88 of the cover slip 86 rests upon the upwardly facing surface of the frame member 56, with the extension section 90 of the cover slip 86 extending beyond the edge of the frame member 56. The wick 98 is then placed upon the edge portion of the cover slip 86 that is opposite to the extension section 90. The cathode 94 is then positioned on the upwardly facing surface of the wick 98 with the cathode's wire extending outwardly from the wick 98 as shown in FIG. 5.

The sample plate 64 is then positioned in the partially assembled plate holder 52. In particular, the front side 128 of the sample plate's support substrate 78 (i.e., the side having the stationary phase 80 disposed thereon) is positioned on the cover slip 86 in a manner which allows the sample plate 64 to be positioned in the recess 72 of the frame member 56. Note that when positioned in the frame member 56 in such a manner, the lower portion 92 of the sample plate 64 extends beyond the bottom edge of the frame member 56.

If used, a sealant may be applied to the sample plate 64 prior to baking and wetting of the plate 64 into the plate holder 52. Specifically, a sealant may be applied to the side edge portions 82, 84 of the support substrate of the sample plate 64 prior to placement of the sample plate 64 onto the cover slip 86. As described above, the sealant may be applied in a manner which may extend a short distance into the stationary phase (i.e., extends into the stationary phase 80 beyond the inner edges of the edge portions 82, 84). It should also be appreciated that a gasket may be used in lieu of a sealant.

Once the sample plate 64 is installed, assembly of the plate holder 52 may be completed. To do so, the frame member 54 is installed. Specifically, the frame member 54 is positioned in contact with the plate member 56 such that the posts 66 are received into the alignment holes 76 defined in the frame member 56. Thereafter, a number of pieces of tape 122 may be used to secure the plate holder 52 together during movement of the plate holder to its test position.

Figure 7:
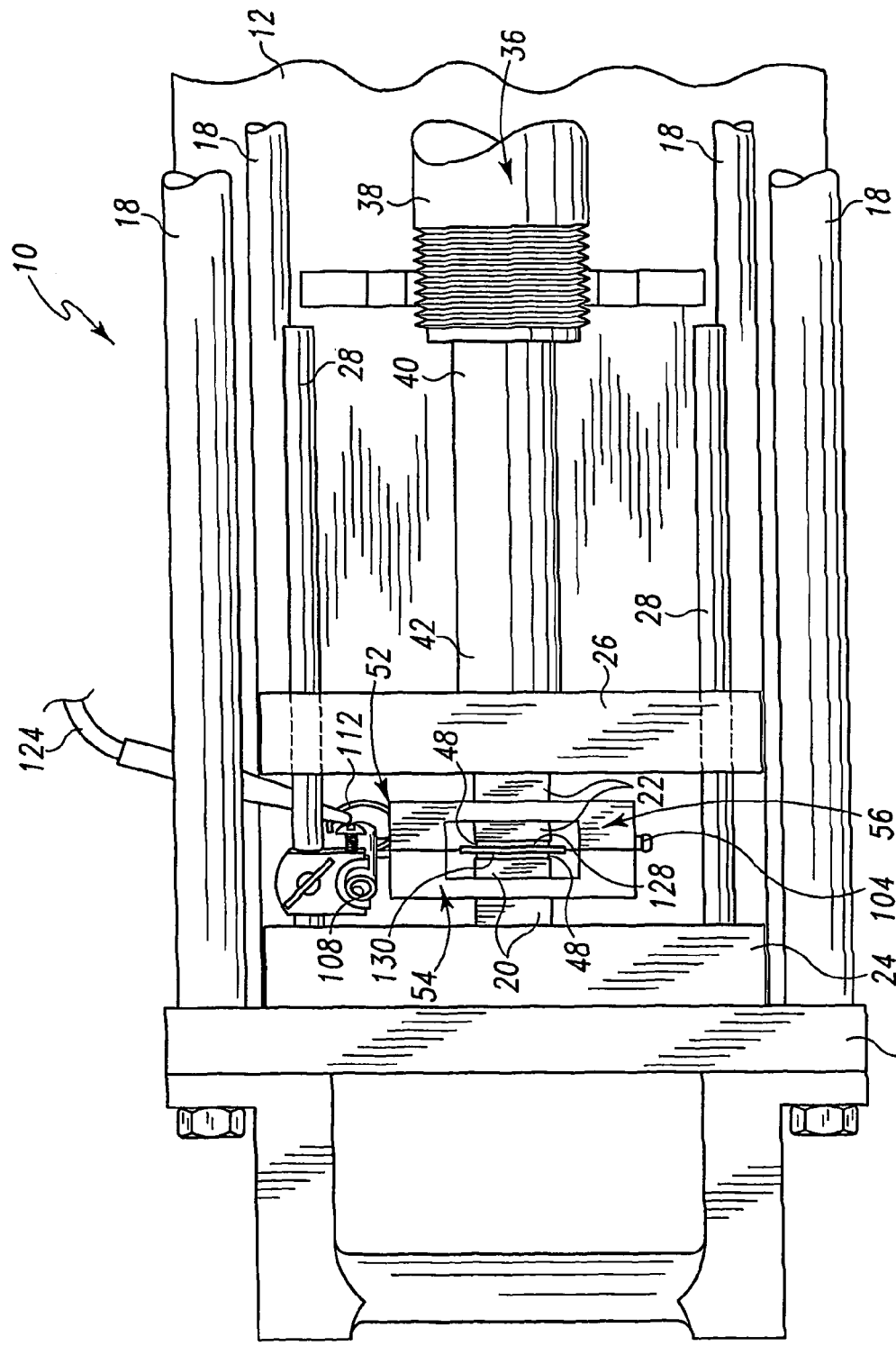
FIG. 7 is a view similar to FIG. 2, but showing the plate holder (with the chromatography sample plate assembled therein) positioned between the die blocks, note that the cover slip, cathode, and the wick have been removed from the plate holder for clarity of description.
Figure 8:
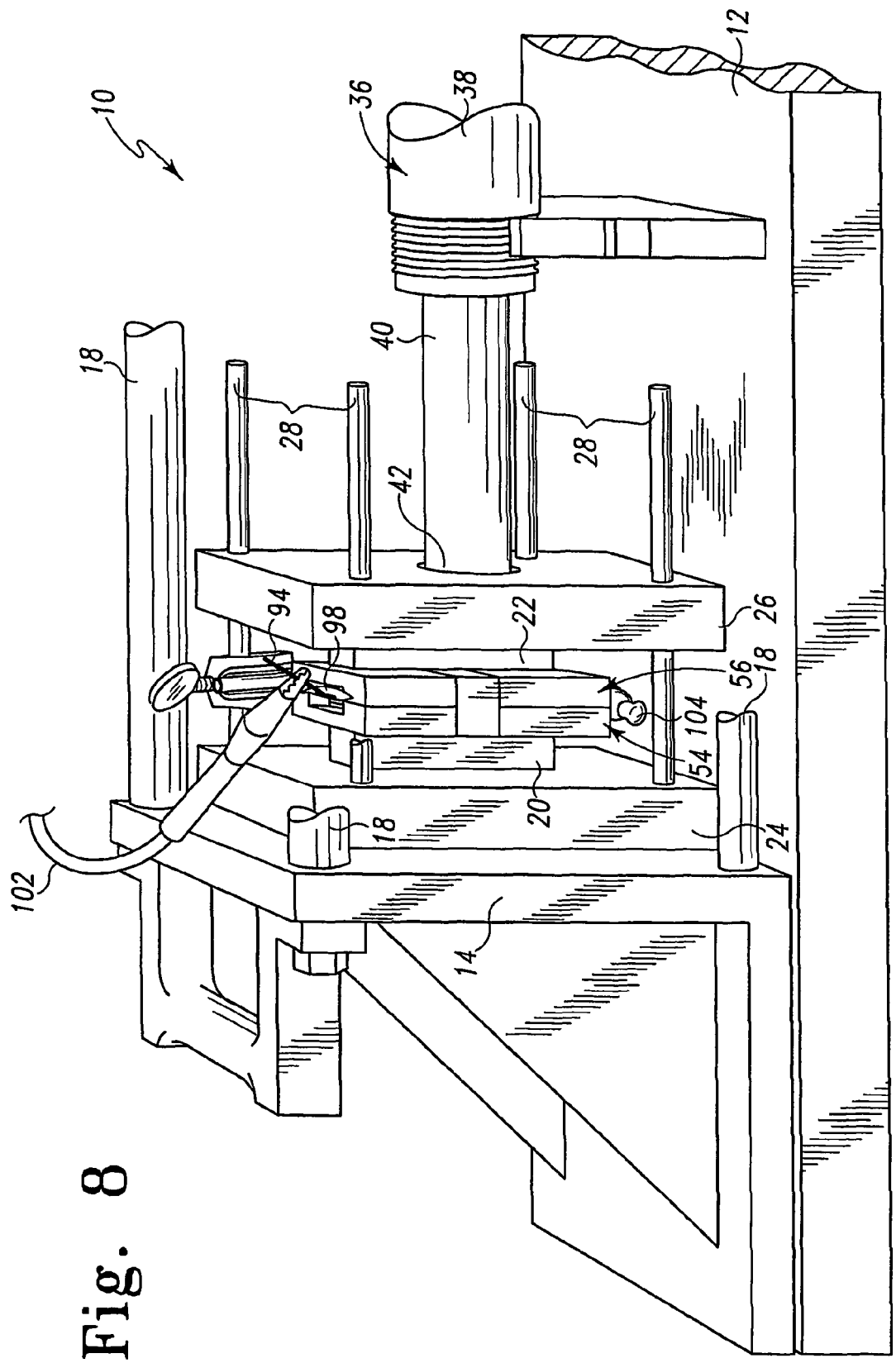
FIG. 8 is a view similar to FIG. 3, but showing the plate holder (with the chromatography sample plate assembled therein) positioned between the die blocks.

The assembled plate holder 52 (with the sample plate 64 secured therein) is then positioned between the die blocks 20, 22. Specifically, the plate holder 52 is advanced into the area between the die blocks 20, 22 with the frame member 54 facing the die block 20. The plate holder 52 is then lowered such that the lower portion 92 of the sample plate 64 and the extension section 90 of the cover slip 86 are advanced through the access opening 106 of the fluid reservoir 104 so as to be exposed to the mobile phase 110 therein. In doing so, a portion of the die block 20 (including the sheet 48 of aluminum nitride ceramic positioned on the face thereof) is received into the opening 58 defined in the body 60 of the frame member 54 as viewed in FIGS. 7 and 8. Note that in such a configuration the aluminum nitride ceramic sheet 48 of the die block 20 contacts the back side 130 of the sample plate 64.

The movable plate 26 (and hence the die block 22 secured thereto) is then advanced toward the plate holder 52. Specifically, the plate 26 is slid along the rods 28 in the general direction of arrow 32 of FIG. 2. Initial advancement of the movable plate 26 may be performed manually (i.e., without the assistance of the fluid ram 36) to align the plate holder 52. In particular, the movable plate 26 may be manually advanced such that the die block 22 is received into the opening 68 defined in the body 70 of the frame member 56. Note that when advanced through the opening 68, the aluminum nitride ceramic sheet 48 of the die block 22 contacts the cover slip 86 covering the front side 128 of the sample plate 64.

Once the plate holder 52 is aligned, the electrodes 94, 112 are electrically coupled to the power source 100. Specifically, the end of the wire associated with the cathode 94 is clipped to the power line 102, and the end of the anode 112 is clipped to the power line 124.

The die block 22 is then urged toward the sample plate 64 positioned in the plate holder 52 so as to exert a force greater than atmospheric pressure thereon. To do so, the user operates the manual fluid pump 44 so as to generate fluid pressure (e.g., hydraulic pressure) therewith. Fluid pressure generated by the manual fluid pump 44 is exerted on the head end (not shown) of the rod 40 of the fluid ram 36 thereby extending the rod 40. During such extension of the rod 40, the rod end 42 of the rod 40 is urged into contact with the side of the movable plate 26 opposite to the die block 22 thereby urging the plate 26 (and hence the die block 22) in the general direction of the arrow 32 of FIG. 2 (i.e., in a direction toward the stationary die block 20). The die block 22 engages the front side 128 of the sample plate 64 (with the cover sheet 86 and aluminum nitride ceramic sheet 48 sandwiched therebetween) and exerts a force thereon. As such, the back side 130 of the sample plate 64 is urged toward the die block 20 (with the aluminum nitride ceramic sheet 48 therebetween).

In such a way, pressure is generated on the sample plate 64. It should be appreciated that the pump 44 and fluid ram 36 may be configured and/or operated to generate any desired pressure on the sample plate 64. In particular, as discussed in the above-incorporated patent (i.e., U.S. Pat. No. 6,303,029), a pressure in the range of 3-90 atmospheres has been suggested for performance of a PPEC procedure. Such pressures are readily generated with the chromatography apparatus 10. It should be appreciated that other pressure ranges may also be generated with the chromatography apparatus 10. For example, pressure in the range of 1.001-120 atmospheres may be utilized in certain test parameters or experimental designs, although substantially higher pressures may be used. Further, it should be appreciated that the concepts of the chromatography apparatus 10 described herein, either with or without some degree of modification, may be utilized to generate any desired test pressures limited only by pressure levels where the sample plate 64 becomes dysfunctional. Moreover, it is contemplated that the pressure exerted on the sample plate 64 may be varied based on the nature of a particular sample or experiment. An increase in pressure typically results in a diminution of electroosmotic flow. There is also a diminution in electrical current for a given applied voltage, and this results in less Joule heating. These effects can be explained by assuming that the increase in pressure causes the average radius of the channels between particles to be diminished. The smaller channels are expected to result in a higher efficiency for PPEC. The diminution in electroosmotic flow can be compensated for by working at a higher applied voltage.

Once a desired test pressure is present on the sample plate, the electrochromatographic procedure may be commenced by actuating the power source 100 so as to create an electrical potential between the cathode 94 and the anode 112, thereby inducing electroosmotic flow to occur. Electroosmotic flow is explained as follows. The particles in the sorbent bed have a high concentration of surface silanol groups, and a large number of these are ionized at the pH used in PPEC. This causes the particles to have a negative charge, and this results in a high concentration of positive ions in the solution adjacent to the particles. These positive ions migrate towards the cathode when an electric field is applied. This results in the bulk flow of liquid towards the cathode. The chemistry of the sorbent particles can be changed such that the surface of the particles has a positive charge. This will result in electroosmotic flow towards the anode.

During such advancement of the mobile phase 110 toward the cathode 94, the components of the sample spot deposited on the sample plate 64 partition between the mobile phase 110 and the stationary phase 80 based upon their differing physical and chemical characteristics. Once the sample spot is separated into its individual components, the resultant separated spots may be detected or visualized by using, for example, a scanning or video densitometer. Raman spectroscopy (with high specificity for identification of individual compounds in the separations matrix) may be used for structural information. Conversely, if the chromatography apparatus 10 is so equipped, the mobile phase 110 may be advanced from the sample plate 64 directly to one or more on-line detectors. Any detector used in HPLC, including a mass spectrometer, could be used for this purpose.

It may be desirable to pre-treat the sample plates 64 prior to the procedure. Specifically, baking or otherwise annealing the plates prior to use may produce enhanced results. Indeed, it has been found that higher baking temperatures (within a prescribed range) produce greater migration distances of the sample spots. For example, a number of the herein described LiChrospher $C_{18}$ plates were baked at various temperatures within the range of 100° C. to 160° C. prior to use. Higher temperatures, with shorter baking times, were also used and found satisfactory. It was observed that the higher the bake temperature, the greater the migration distance of the sample spots for a given set of experimental conditions. There is a linear relationship, between migration distance in PPEC and the baking temperature, for the LiChrospher plates baked for twenty minutes at temperatures between 100° C. and 160° C. Other types of plates may have a non-linear relationship.

The electric current (and Joule heating) during PPEC may be reduced by pretreatment of the TLC plate. This allows PPEC to be performed at a higher electric field (i.e. at a higher applied voltage) than is possible without this pretreatment. An example of such a pretreatment is to first bake the plate in an oven at 160° C. for 20 minutes, to then immerse the TLC plate in 70% aqueous ethanol containing 0.01 M hydrochloric acid for five minutes at room temperature. The plate is then immersed in pure water for five minutes, and then placed in an oven at 100° C. for five minutes. The edges of the plate are then scraped and treated with sealant as described herein. It is then baked again for 20 minutes at 160° C.

In addition to the aforedescribed structure and operation, the chromatography apparatus 10 may be embodied and operated in a number of additional manners. For example, the apparatus 10 may be modified to include a reservoir similar to the reservoir 104 at the opposite end of the sample plate 64 (i.e., at the top of the sample plate 64 as viewed in the orientation of FIG. 8). In such a case, the upper portion 96 of the front side 128 of the sample plate 64 (i.e., the side having the stationary phase 80 disposed thereon) would be positioned in contact with the mobile phase contained in such an additional reservoir much in the same way the lower portion 92 of the plate 64 contacts the mobile phase 110 contained in the reservoir 104. In such-an arrangement, the cathode may be embodied as a piece of stainless steel or platinum wire positioned in the additional reservoir.

Figure 9:
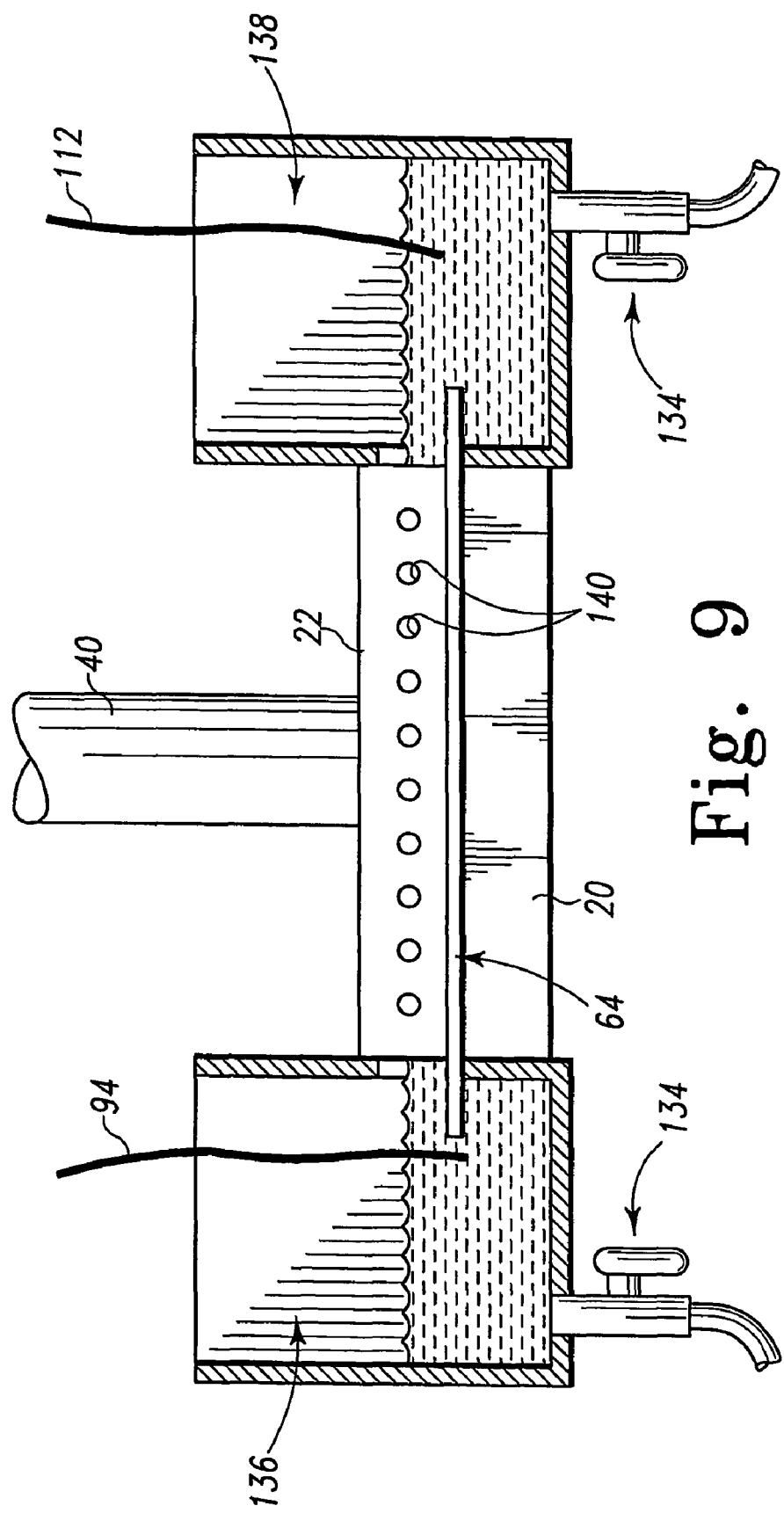
FIG. 9 is a diagrammatic view showing a chromatography apparatus configured to exert pressure on a horizontally-oriented chromatography sample plate.

As shown in FIG. 9, the chromatography apparatus may be embodied with the sample plate 64 mounted in a horizontal arrangement. Note that in the diagrammatic view of FIG. 9, only the sample plate 64 and the die blocks 20, 22 are shown with the remaining components of the apparatus being removed for clarity of description. In this arrangement, a fluid reservoir 136, 138 is positioned on each end of the plate 64. The cathode may be positioned in one of the reservoirs 136, 138, with the anode being positioned in the other. Each of the fluid reservoirs 136, 138 may be rapidly drained through a quick drain valve 134. Note that the upper die block 22 is shown with a number of coolant passages 140 defined therein for cooling the die block 22 during a chromatography procedure.

Figure 11:
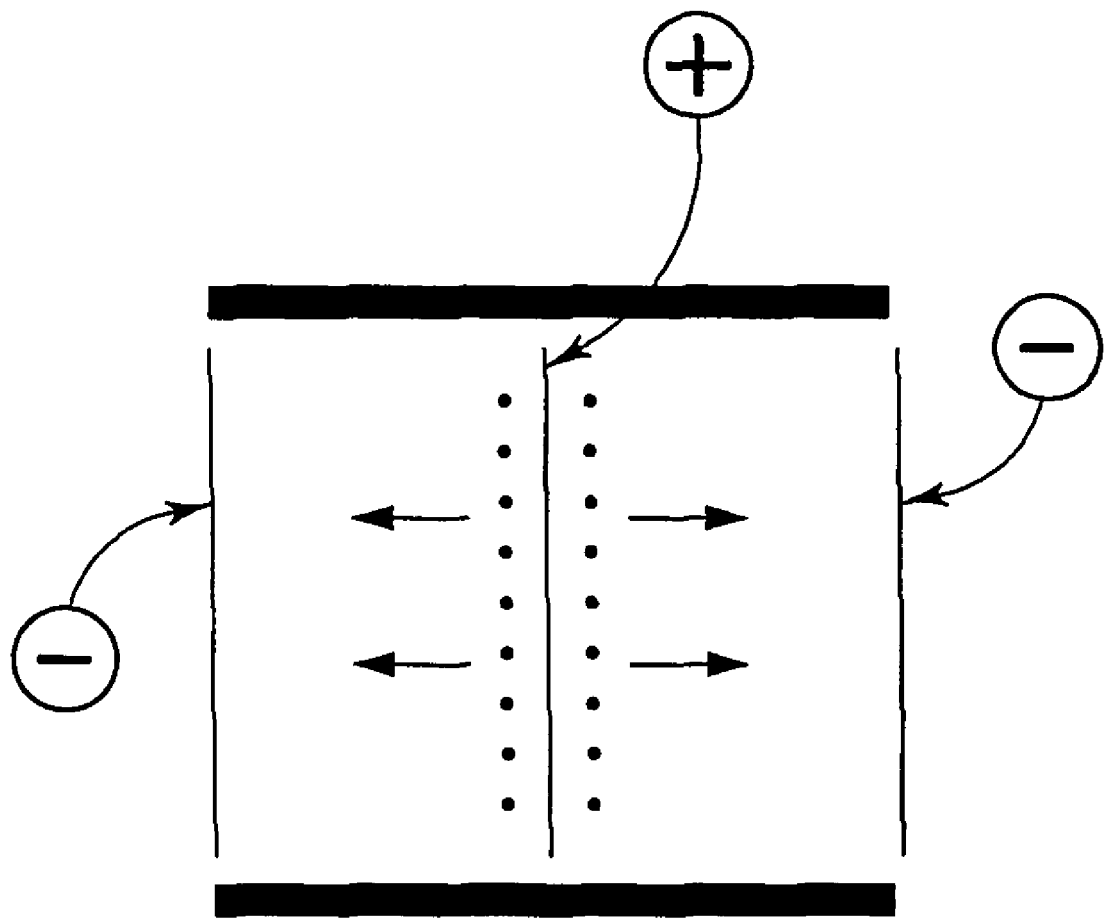
FIG. 11 is a diagrammatic view which illustrates a two-directional chromatographic procedure.
Figure 12:
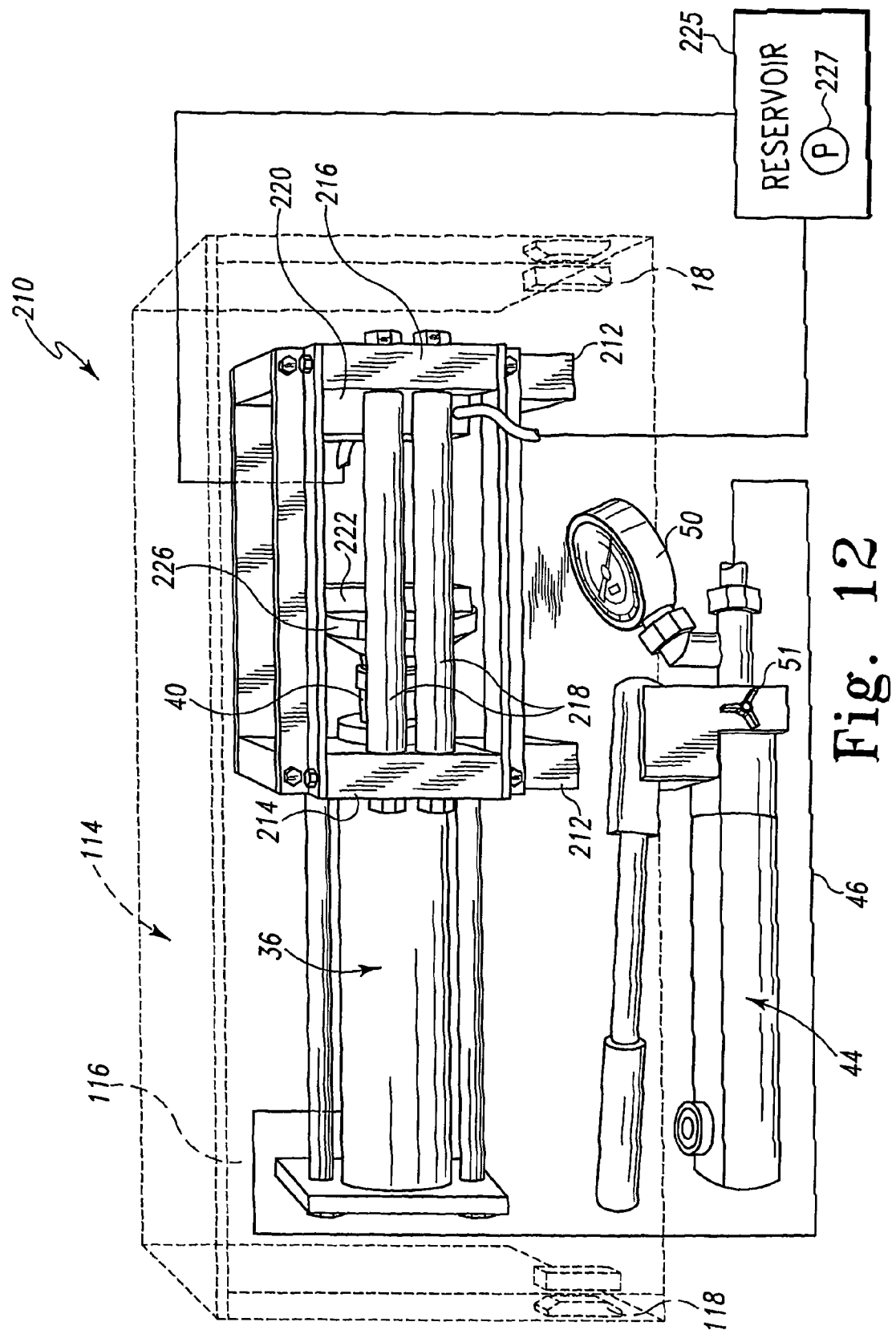
FIG. 12 is a perspective view of another chromatography apparatus for performing a PPEC procedure.
Figure 13:
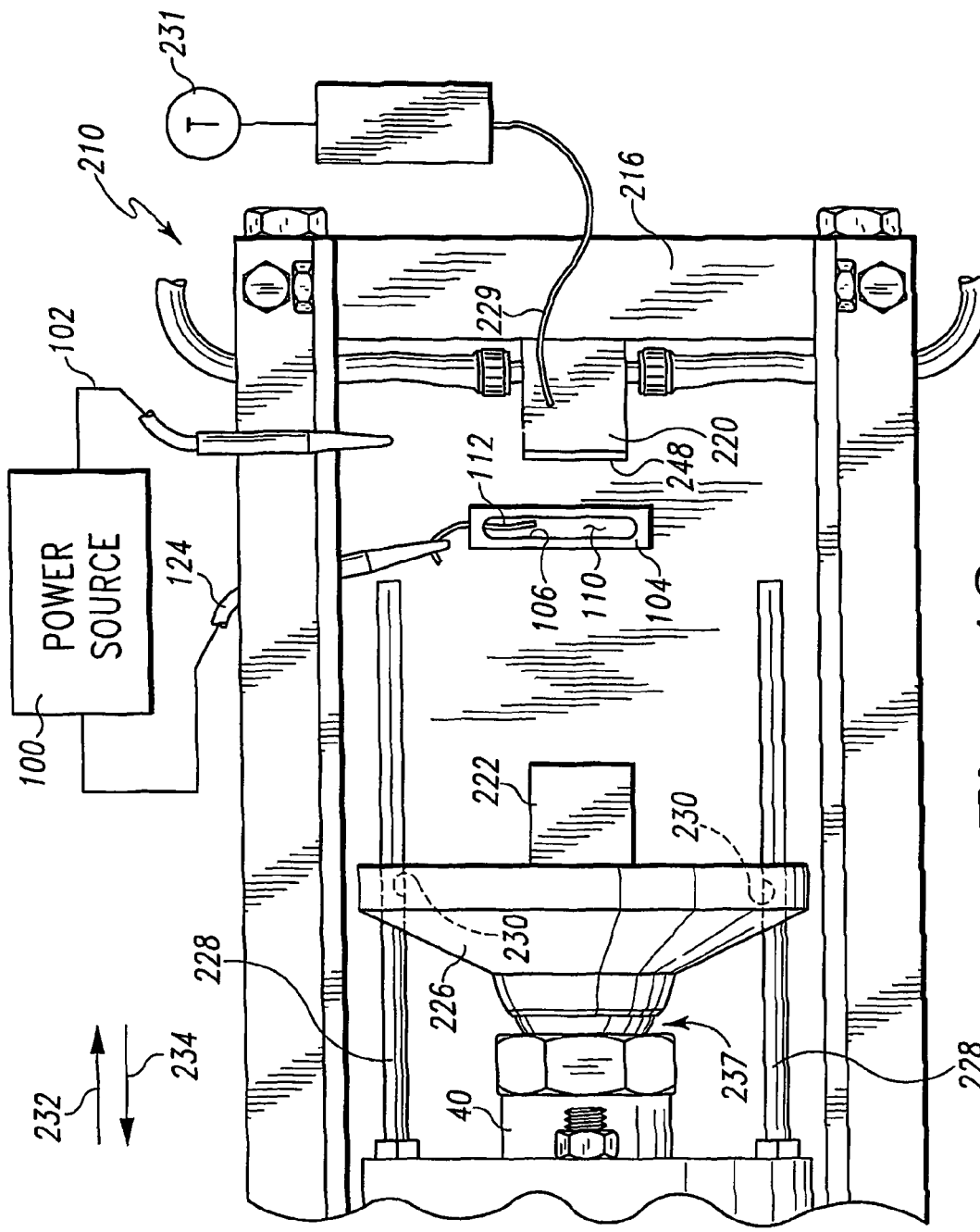
FIG. 13 is an enlarged fragmentary plan view of the chromatography apparatus of FIG. 12.
Figure 14:
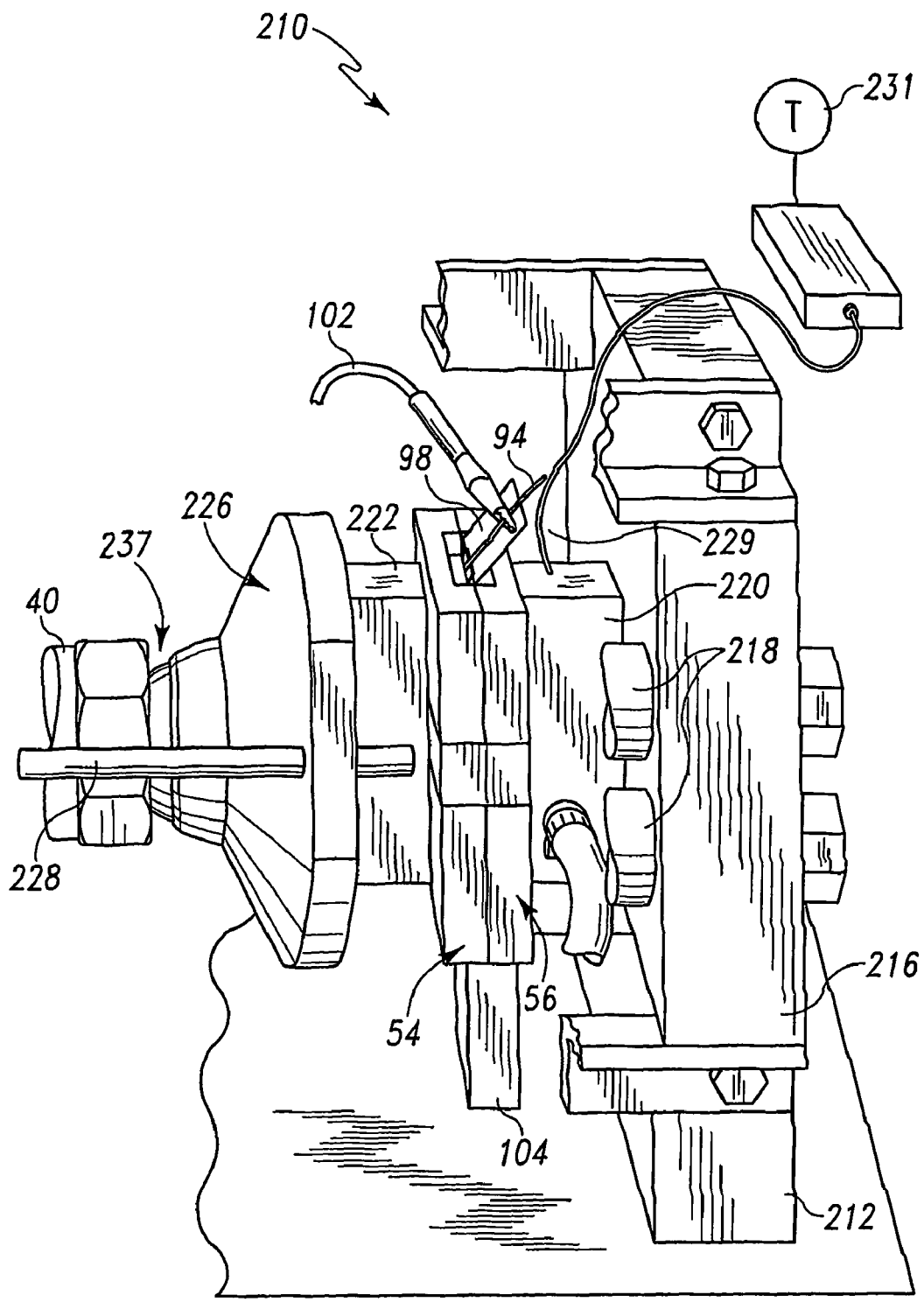
FIG. 14 is an enlarged fragmentary view of the chromatography apparatus of FIG. 12 showing the plate holder (with the chromatography sample plate assembled therein) positioned between the die blocks.

Referring now to FIGS. 12-14, there is shown another embodiment of the chromatography apparatus 10 (designated with reference numeral 210). Similar reference numerals are used in FIGS. 12-14 to designate components which are similar to those discussed in regard to FIGS. 1-13. The chromatography apparatus 210 includes a pair of support blocks 212 having a pair of upwardly extending support plates 214, 216 secured thereto. A number of struts 218 are secured to each of the support plates 214, 216. As shown in FIG. 12, the chromatography apparatus 210 also includes a pair of die blocks 220, 222. In the exemplary embodiment described herein, each of the die blocks 220, 222 has a width of 2.5 cm. The die block 220 is secured to the support plate 216.

The die block 222 is secured to a movable plate 226. The die block 222 is movable relative to the die block 220. In particular, the support plate 214 has a number of rods 228 extending therefrom. The movable plate 226 has a corresponding number of holes 230 defined therein into which the rods 228 are received. As such, the movable plate 226, and hence the die block 222, may slide back and forth along the rods 228 in a direction toward the die block 220 (as indicated by the arrow 232 of FIG. 13) and in a direction away from the die block 220 (as indicated by the arrow 234 of FIG. 13).

Figure 15:
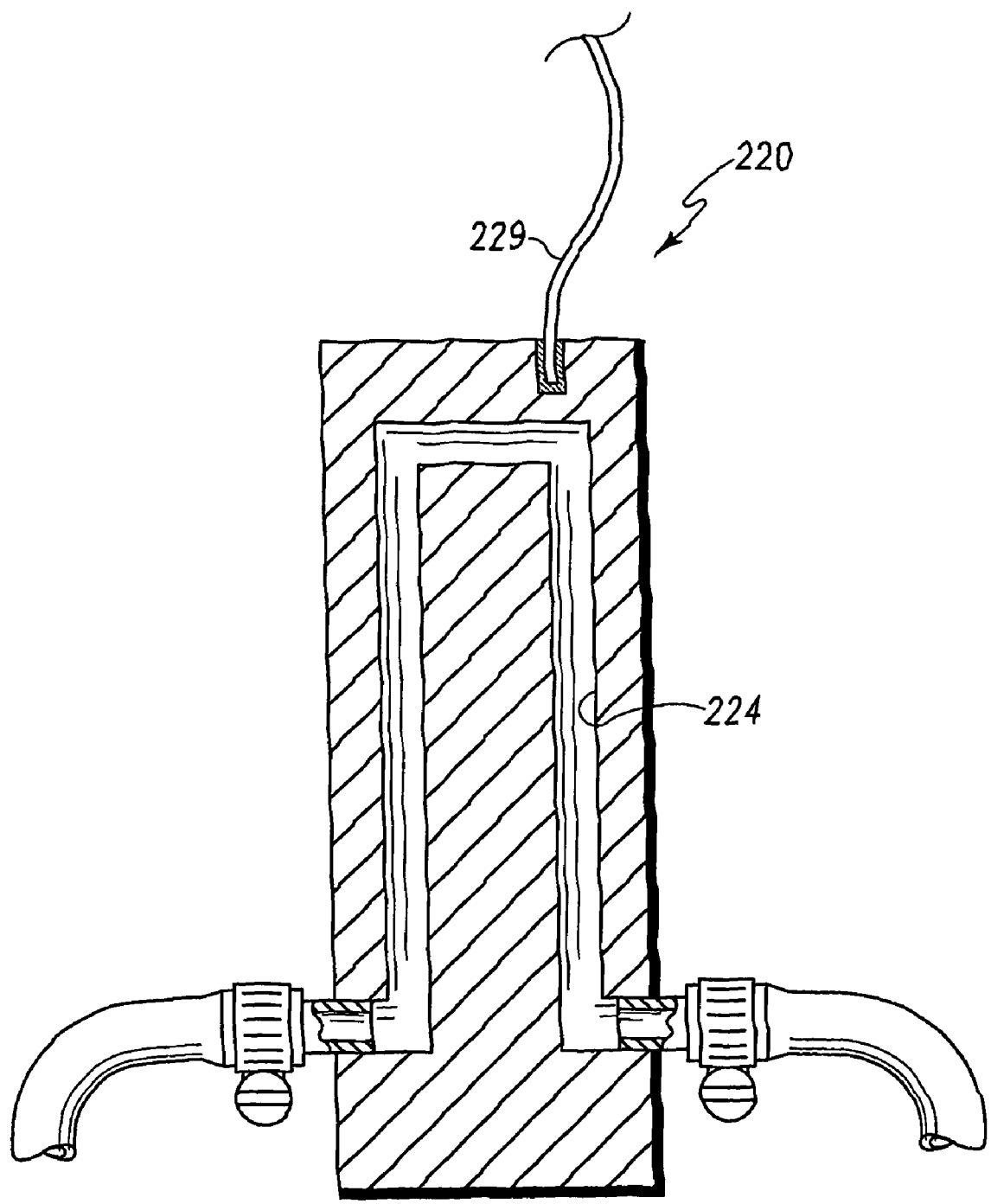
FIG. 15 is a cross sectional view of one of the die blocks showing the fluid channels formed therein.

The stationary die block 220 has a number of fluid passages 224 formed therein (see FIG. 15). A fluid, such as a coolant (e.g., water), may be advanced through the passages 224 from a reservoir 225 and thereafter returned to the reservoir 225 to cool the die block 220 thereby enhancing the heat sink capabilities of the die block 220. A pump 227 may be used to advance the fluid in such a manner. Use of a fluid (e.g., a coolant) allows a sample plate to be maintained at a desired temperature including room temperature (or temperatures above or below room temperature) during a procedure. As such, the fluid may be used to cool a sample plate or maintain the plate at a desired constant temperature. Moreover, fluid passages could be utilized in the die block 220 to create a temperature gradient along the sample plate's axis of mobile phase travel. Typically, the direction of electroosmotic flow is toward the colder part of the gradient. It has been suggested that the formation of such a temperature gradient may generate sharpened peaks during sample analysis (which will lead to enhanced peak resolution). It should be appreciated that the fluid passages 224 in the die block 220 may be utilized to circulate a heated fluid so as to heat the sample plate, if desired.

As shown in FIG. 13, a thermocouple 229 extends into the die block 220. The thermocouple 229 is used to sense or otherwise determine the temperature of the die block 220. The thermocouple 229 is electrically coupled to a temperature meter 231. As such, the temperature of the die block 220 may be output to a user.

As shown in FIG. 13, a thermally conducting, electrically insulating sheet 248 may be positioned on the face of the die block 220. The sheet 248 is a thermal conductor thereby allowing heat on a sample plate to be transferred to the die block 220. The sheet 248 is also an electrical insulator thereby electrically insulating the sample plate from the die block 220. The sheet 248 may be constructed with a variety of materials having such characteristics. One material which may be utilized in the construction of the sheet 248 is a thin sheet of aluminum nitride ceramic. In the exemplary embodiment described herein, the sheet 248 is attached to the face of the die block 220 with drops of mineral oil. A piece of polymeric material such as Delrin®, which is commercially available from E.I. du Pont de Nemours and Company of Wilmington, Del., or other material (not shown) may be installed on the bottom surface of the die block 220 in a manner which forms a lip on which the bottom of the sheet 248 rests. Such a lip facilitates maintenance of the sheet 248 in a desired location on the face of the die block 220. It should be appreciated that in certain configurations the sheet 248 may not be used. It should also be appreciated that a sheet 248 may be secured to the face of the die block 222. The sheet attached to the die block 222 may be formed of other materials such as glass.

The fluid ram 36 is utilized to urge the movable plate 226 (and hence the die block 222) in the general direction of the arrow 232 (i.e., toward the stationary die block 220). Specifically, the rod 40 of the fluid ram 36 is coupled to the movable plate 226 by a swivel joint 237. As such, during extension of the rod 40, the movable plate 226 (and hence the die block 222) is urged in the general direction of the arrow 232 of FIG. 13 (i.e., in a direction toward the stationary die block 220). As with the apparatus 10, operation of the manual fluid pump 44 generates fluid pressure within a fluid line 46 thereby causing extension of the rod 40 in such a manner.

The plate holder 52 may be used to support sample plates in the apparatus 210. Specifically, as shown in FIG. 14, the sample plate 64 may be positioned between the die blocks 220, 222 by use of the plate holder 52.

As with the chromatography apparatus 10, the apparatus 210 includes an enclosure or housing 114. The housing 114 surrounds the sample during performance of a chromatographic procedure.

To perform a electrochromatography procedure with the chromatography apparatus 210, the sample plate 64 is first wetted and then installed into the plate holder 52. To do so, as shown in FIG. 5, the frame member 56 may be positioned on a flat surface with the surface of the frame member's body 70 having the holes 76 defined therein facing upwardly. The cover slip 86 is then positioned on the upwardly facing surface of the frame member 56. Note that the main body 88 of the cover slip 86 rests upon the upwardly facing surface of the frame member 56, with the extension section 90 of the cover slip 86 extending beyond the edge of the frame member 56. The wick 98 is then placed upon the edge portion of the cover slip 86 that is opposite to the extension section 90. Note that as shown in FIG. 14, the wick 98 may be embodied in a generally rectangular-shaped configuration (i.e., without the arcuate-shaped upper portion). The cathode 94 is then positioned on the upwardly facing surface of the wick 98 with the cathode's wire extending outwardly from the wick 98 as shown in FIG. 5.

The sample plate 64 is then positioned in the partially assembled plate holder 52. In particular, the front side 128 of the sample plate's support substrate 78 (i.e., the side having the stationary phase 80 disposed thereon) is positioned on the cover slip 86 in a manner which allows the sample plate 64 to be positioned in the recess 72 of the frame member 56. Note that when positioned in the frame member 56 in such a manner, the lower portion 92 of the sample plate 64 extends beyond the bottom edge of the frame member 56.

If used, a sealant may be applied to the sample plate 64 prior to baking and wetting of the plate 64 into the plate holder 52. Specifically, a sealant may be applied to the side edge portions 82, 84 of the support substrate of the sample plate 64 prior to placement of the sample plate 64 onto the cover slip 86. As described above, the sealant may be applied in a manner which may extend a short distance into the stationary phase (i.e., extends into the stationary phase 80 beyond the inner edges of the edge portions 82, 84). It should also be appreciated that a gasket may be used in lieu of a sealant.

Once the sample plate 64 is installed, assembly of the plate holder 52 may be completed. To do so, the Same member 54 is installed. Specifically, the frame member 54 is positioned in contact with the plate member 56 such that the posts 66 are received into the alignment holes 76 defined in the frame member 56. Thereafter, a number of pieces of tape 122 may be used to secure the plate holder 52 together during movement of the plate holder to its test position.

The assembled plate holder 52 (with the sample plate 64 secured therein) is then positioned between the die blocks 220, 222. Specifically, the plate holder 52 is advanced into the area between the die blocks 220, 222 with the frame member 56 facing the die block 220. The plate holder 52 is then lowered such that the lower portion 92 of the sample plate 64 and the extension section 90 of the cover slip 86 are advanced through the access opening 106 of the fluid reservoir 104 so as to be exposed to the mobile phase 110 therein. In doing so, a portion of the die block 220 (including the sheet 48 of aluminum nitride ceramic positioned on the face thereof) is received into the opening 68 defined in the body 70 of the frame member 56. Note that in such a configuration the aluminum nitride ceramic sheet 248 of the die block 220 contacts the cover slip 86 covering the front side 128 of the sample plate 64.

The movable plate 226 (and hence the die block 222 secured thereto) is then advanced toward the plate holder 52. Specifically, the plate 226 is advanced along the rods 228 in the general direction of arrow 232 of FIG. 13 by initial operation of the fluid ram 36. Note that when advanced through the opening 58 of the frame member 54, the die block 222 (or the glass or aluminum nitride sheet secured thereto) contacts the back side 130 of the sample plate 64.

Once the plate holder 52 is aligned, the electrodes 94, 112 are electrically coupled to the power source 100. Specifically, the end of the wire associated with the cathode 94 is clipped to the power line 102, and the end of the anode 112 is clipped to the power line 124.

The die block 222 is then urged toward the sample plate 64 positioned in the plate holder 52 so as to exert a force greater than atmospheric pressure thereon. To do so, the user operates the manual fluid pump 44 so as to generate fluid pressure (e.g., hydraulic pressure) therewith. Fluid pressure generated by the manual fluid pump 44 is exerted on the head end (not shown) of the rod 40 of the fluid ram 36 thereby extending the rod 40. During such extension of the rod 40, the rod 40 urges the plate 226 (and hence the die block 222) in the general direction of the arrow 232 of FIG. 13 (i.e., in a direction toward the stationary die block 220). The die block 220 engages the front side 128 of the sample plate 64 (with the cover sheet 86 and aluminum nitride ceramic sheet 48 sandwiched therebetween) and exerts a force thereon.

In such a way, pressure is generated on the sample plate 64. It should be appreciated that the pump 44 and fluid ram 36 may be configured and/or operated to generate any desired pressure on the sample plate 64. In particular, as discussed in the above-incorporated patent (i.e., U.S. Pat. No. 6,303,029), a pressure in the range of 3-90 atmospheres has been suggested for performance of a PPEC procedure. Such pressures are readily generated with the chromatography apparatus 210. It should be appreciated that other pressure ranges may also be generated with the chromatography apparatus 210. For example, pressure in the range of 1.001-120 atmospheres may be utilized in certain test parameters or experimental designs, although substantially higher pressures may be used. Further, it should be appreciated that the concepts of the chromatography apparatus 210 described herein, either with or without some degree of modification, may be utilized to generate any desired test pressures limited only by pressure levels where the sample plate 64 becomes dysfunctional. Moreover, it is contemplated that the pressure exerted on the sample plate 64 may be varied based on the nature of a particular sample or experiment. An increase in pressure typically results in a diminution of electroosmotic flow. There is also a diminution in electrical current for a given applied voltage, and this results in less Joule heating. These effects can be explained by assuming that the increase in pressure causes the average radius of the channels between particles to be diminished. The smaller channels are expected to result in a higher efficiency for PPEC. The diminution in electroosmotic flow can be compensated for by working at a higher applied voltage.

Once a desired test pressure is present on the sample plate, the electrochromatographic procedure may be commenced by actuating the power source 100 so as to create an electrical potential between the cathode 94 and the anode 112, thereby inducing electroosmotic flow to occur. During advancement of the mobile phase 110 toward the cathode 94, the components of the sample spot deposited on the sample plate 64 partition between the mobile phase 110 and the stationary phase 80 based upon their differing physical and chemical characteristics. Once the sample spot is separated into its individual components, the resultant separated spots may be detected or visualized by using, for example, a scanning or video densitometer. Raman spectroscopy (with high specificity for identification of individual compounds in the separations matrix) may be used for structural information. Conversely, if the chromatography apparatus 10, 210 is so equipped, the mobile phase 110 may be advanced from the sample plate 64 directly to one more on-line detectors. Any detector used in HPLC, including a mass spectrometer, could be used for this purpose.

During performance of the test procedure, the temperature of the sample plate 64 may be controlled by advancing fluid (e.g., water) through the passages 224 defined in the die block 220. For example, the sample plate 64 may be cooled by advancing coolant through the fluid passages 224. The output of the thermocouple 229 may be monitored to determine the temperature of the die block 220 as displayed on the temperature meter 231.

It should be appreciated that the chromatography apparatus 10, 210 may be configured to accommodate sample plates of various sizes and configurations. For example, although the sample plate 64 described herein is shown as a 12 cm×3.3 cm plate, other configurations are contemplated. For example, a 20 cm×20 cm sample plate may be utilized. To do so, the configuration of the die blocks 20, 22 may be modified to accommodate the size and shape of the sample plate. In the case of use of such sample plates, numerous samples may be spotted in a side-by-side arrangement. In one exemplary embodiment, thirty-eight samples may be spotted side-by-side on a 20 cm×20 cm sample plate.

Figure 10:
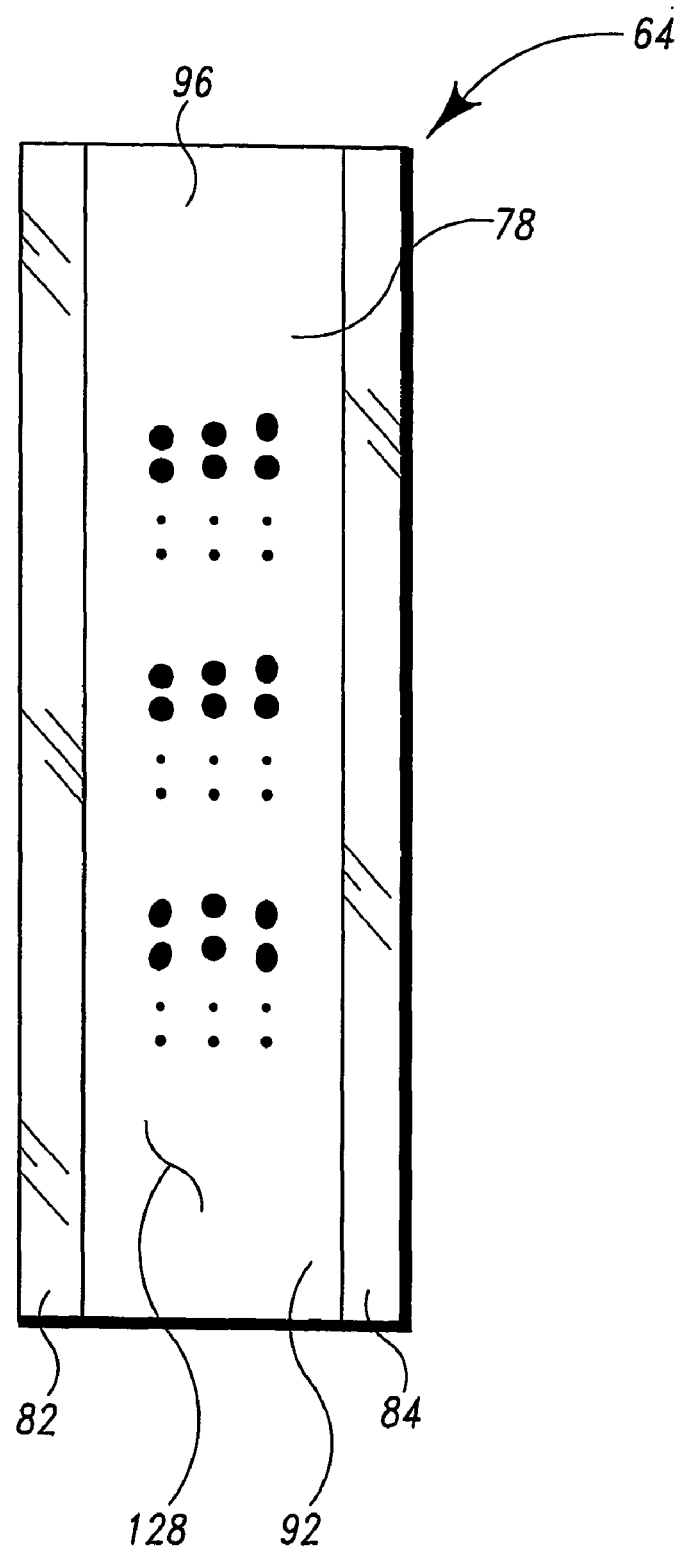
FIG. 10 is a plan view of a sample plate, after being subjected to a chromatographic procedure, having a number of sample spots "stacked" thereon.

Moreover, as shown in FIG. 10, sample spots may be "stacked" in the vertical direction. For example, three rows of three samples each may be arranged on a single 12 cm×3.3 cm plate. Moreover, if four samples are stacked vertically on a 20 cm wide plate, one hundred fifty-two samples (i.e., 4×38 samples) may be simultaneously separated. When stacking samples on a sample plate, the spots may be deposited onto a dry sample plate. The plate is then dipped or otherwise pre-wetted with mobile phase, and thereafter subjected to the chromatographic procedure.

The chromatography apparatus 10, 210 may also be utilized to perform two-dimensional chromatography. In such a case, a square-shaped sample plate may be used. To do so, sample spots are deposited on to the sample plate and developed under pressure as described above. The sample plate is then removed from the apparatus, rotated 90°, reinserted into the apparatus, and developed a second time with a mobile phase of a different chromatographic selectivity.

PPEC may also be performed in the two-directional mode as illustrated in FIG. 11. The mobile phase is in electrical contact with the anode, and is introduced along a line at the center of the TLC plate. The samples are spotted on either side of this line and migrate towards the two cathodes as illustrated in FIG. 11. An alternative configuration is also possible where the mobile phase flows from the two sides of the plate towards the center of the plate where the mobile phase enters a channel. The mobile phase in the channel is in electrical contact with the cathode and the mobile phase entering the sides of the TLC plate is in electrical contact with the anode. In this configuration sample spots are placed along line close to each edge of the TLC plate.

Although the chromatography apparatus 10, 210 has herein been described with one movable die block (i.e., the die block 22, 222) and one stationary die block (i.e., the die block 20, 220), it should be appreciated that other configurations are contemplated. For example, both die blocks 20, 22 and 220, 222 may be movable.

Although the compression surface into which the sample plate 64 is urged is herein exemplary described as a die block (i.e., the die block 20) which is similar in shape to the movable die block (i.e., the die block 22), it should be appreciated that any type or configuration of compression surface may be utilized.

In addition to fluid rams (e.g., hydraulic or pneumatic), other devices may be used to move the movable plate 26, 226. For example, a worm shaft or ratchet mechanism driven by a manual crank or an electric motor may be used to urge the movable plate 26, 226 toward the sample plate 64. Moreover, an electric pump may be used to urge the movable plate 26, 226 toward the sample plate 64. Moreover, pressure actuators based on either a piezo-electric transducer or a linear electro-magnetic displacement device would serve as well with respect to the PPEC technique. The application of these technologies may result in a more compact apparatus.

Moreover, although the cathode 94 is herein described as being located at the top of the apparatus (as viewed in the orientation of FIGS. 8 and 14) with the anode 112 located at the bottom of the apparatus (as viewed in the orientation of FIGS. 8 and 14), other configurations are contemplated. For example, the polarity of the electrodes 94, 112 may be reversed based on a particular design of the apparatus or plate. In essence, if desired, the apparatus may be configured to advance the mobile phase 110 in any desired direction.

The plate holder 52 may be embodied in other configurations. For example the plate holder may be embodied as an electrically insulated recessed surface defined in one of the die blocks 20, 22, 220, 222. The sample plate 64 would be positioned in such a recessed surface during a procedure.

The position of the plate holder 52 may also be reversed within the apparatus. Specifically, in the case of the apparatus 10, the plate holder 52 may be positioned such that the movable die block 22 contacts the back side 130 of the sample plate 64 so as to urge the front side 128 of the sample plate 64 into contact with the stationary die block 20. Likewise, the plate holder 52 may also be reversed during use with the apparatus 210.

An apparatus may be constructed to pre-wet the sample plates. In one exemplary design of such an apparatus, solvent is forced upward through a small channel defined by two glass slides separated by about 1 mm. The slide assembly is somewhat wider than the width of the sample plate. A "fountain" of solvent, having a height of about 2 to 3 mm, appears at the top of the slit if the solvent is under slight positive pressure. This fountain will form a uniform wave across its width. Solvent will be permitted to flow away from the fountain (by gravity)

to a reservoir below. It may then be recovered and recirculated back to a pump. In such a configuration, the sample plate may be placed on a slightly inclined track in a suitable carrier. The surface of the sample plate will be oriented downward. The carrier slides down the inclined track at a constant rate over the solvent fountain under gravitational acceleration. Motion of the plate could also be accomplished by means of a motorized or other type of device. When properly adjusted, the sample plate's sorbent layer surface will pass through the top of the wave of the fountain. The motion of the plate carrier is configured to distribute solvent in a desired direction, without solvent runoff toward the edges of the plate. The rate of travel across the fountain may be controlled by the inclination of the track.

The surface of the ram assembly that bears on the sample plate may be coated with a polymer or other deformable material in order to produce a more uniform pressure on the sample plate. In one embodiment, a non-Newtonian polymer having a tendency to become less viscous under greater pressure may be applied to the end of the ram's rod. During operation of the apparatus, local high pressure points across the sample plate will create slightly less viscous regions on the applied polymer film. These regions will not support a sheer stress as well as adjacent areas. There will be a slight flow of polymer along the pressure gradient, thus pressure will be more uniformly equalized on the sample plate.

The concepts of the present disclosure may also be utilized for preparative TLC. This can be performed with a 1 mm thick preparative layer although a thicker layer may also be contemplated. A low buffer concentration may be used to reduce the amount of Joule heating.

In principal, the TLC layer may be prepared on a very thin glass backing or on a material such as aluminum nitride ceramic. This would allow heat to be removed from both sides of the sorbent layer.

Two parallel channels, coated with insulating material, may be formed in the pressurized block (e.g. the die block 22). Fluid (e.g., mobile phase) may be delivered to the sorbent layer of the sample plate via these channels. The electrodes (i.e., the anode and cathode) may also be positioned in these channels. Such a design will allow mobile phase to be pumped through the channels and this would allow a mobile phase gradient to be run.

Moreover, the mobile phase may be delivered via a tube, constructed of an electrically insulating material, with a slit formed therein. The anode, or a portion thereof, may be positioned within the tube. The bottom edge of the plate may be placed through this slit into the tube. This arrangement allows for liquid (e.g., mobile phase) to be pumped through the tube and for a solvent gradient to be delivered to the sorbent layer. A similar arrangement may be used for the cathode end of the plate, with a seal being used around the slit to prevent leakage. Such an arrangement may also be used with the TLC plate in a horizontal position.

In a further modification of this arrangement such a tube (having a slit formed therein) may be secured to, or formed in, each end of a polymer sheet or block that covers the sorbent layer. As before, the anode and the cathode may be positioned, respectively, in these tubes. Mobile phase is delivered to the sorbent layer through the slit, travel through the sorbent layer, and exits through the slit formed in the other tube (i.e., the tube having the cathode).

As such, it should be appreciated from the above discussion that the mobile phase may be conveyed to the plate(s) via a any of a number of different embodiments of a solvent channel. This channel may be open to the ambient environment or sealed depending on the orientation of the plate and the mobile phase relative to a vertical reference. In addition, the plate may be fabricated such that it its edges are immersed directly into the channel, or they are immersed in the mobile phase via right-angle structures on the edges of the plate(s). Thus, separation may be achieved with numerous orientations of the plate(s).

The plate holder 52 may be configured as a cassette. In such a way, this cassette may be easily loaded into and out of the apparatus 10, 210.

PPEC may also be performed with non-aqueous mobile phases on a silica stationary phase, i.e. in the normal phase mode. Normal phase separations may be performed using an ionic liquid as a component of the mobile phase (this has been reported in LC/GC magazine—volume 21, page 884, 2003—for non-aqueous capillary electrophoresis (CE) using 1-butyl-3-methylimidazolium ionic liquid). PPEC may also be performed in the normal phase mode with a mobile phase containing a suitable concentration of water and/or other polar solvent. PPEC may also be performed with any combination of stationary and mobile phase that is used in Capillary Electrochromatography (CEC).

A TLC layer may consist of fused silica particles, quartz particles or glass particles or other particles having a similar surface chemistry. These particles may be held together by sintering or by some other technique, or may be without any binding. The surface of these particles will resemble the surface of the capillary tube used in capillary electrophoresis (CE), and it will be possible to perform PPEC in a manner that is analogous to CE in a planar format. This will allow for the parallel separation of proteins and other macromolecules, and, in contrast to CE, will allow for the preparative separations of such compounds.

In lieu of the sealing techniques described above, the chromatography apparatus 10, 210 may be modified by the addition of capture grooves to the fixed and moveable pressure plates 24, 26 to accommodate a properly sized O-ring. The O-ring material will be properly formulated to provide enhanced chemical resistance depending on the nature of the reagents required in a particular chemical separation system.

Active temperature control of the separation medium may be achieved by any of several methods that are inherently adaptable to active feedback control. The plates can be heated or cooled by providing passages to circulate a heat exchange fluid. The fluid may be actively heated above or cooled below ambient temperature by an external heat exchanger. The plates may be proportionally controlled by the combination of a low temperature heat exchange fluid and an array of resistive heaters on the pressure plates. This later method would be particularly adaptable to precise proportional temperature control. The pressure plates could also be cooled or heated by the installation of thermo-electric devices that operate via the Peltier effect. In this example, it would not be necessary to circulate a heat exchange fluid.

It should be appreciated that a plate holder may be used which accommodates a plurality of sample plates. In such an arrangement, the compressive forces are transferred from one plate to another. Moreover, in certain embodiments, a heat exchange block (i.e., a block having fluid channels formed therein) may be positioned between adjacent sample plates.

Moreover, it should also be appreciated that two sample plates may be positioned back-to-back in the plate holder thereby allowing both plates to be run during the same cycle of the apparatus. In addition, a single sample plate may have stationary phase disposed on both sides thereof.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the concepts of the present disclosure arising from the various features of the systems described herein. It will be noted that alternative embodiments of each of the systems of the present disclosure may not include all of the features described yet still benefit from at least some of the advantages of such features. Those of ordinary skill in the art may readily devise their own implementations of a system that incorporate one or more of the features of the present disclosure and fall within the spirit and scope of the invention as defined by the appended claims.

The invention claimed is:

1. A method of performing electrochromatography, the method comprising the steps of:
    positioning a sample plate in a plate holder;
    positioning a frame member in contact with the plate holder to form an assembled plate holder;
    positioning the assembled plate holder between a pair of die blocks;
    urging a die block of the pair of die blocks with a ram through an opening defined in the body of the frame member toward a stationary phase supported on the sample plate so as to exert a pressure which is greater than atmospheric pressure against the stationary phase; and
    creating an electrical potential across the stationary phase with a first electrode and a second electrode so as to cause a liquid mobile phase to be advanced across the stationary phase.

2. The method of claim 1, further comprising the step of placing the stationary phase in contact with the liquid mobile phase prior to the creating step.

3. The method of claim 1, wherein urging the die block toward a stationary phase supported on the sample plate comprises urging a metal die block toward the stationary phase supported on the sample plate.

4. The method of claim 1, further comprising the step of positioning the sample plate in a plate holder prior to the urging step.

5. The method of claim 1, wherein the urging step comprises urging the die block with a fluid ram.

6. The method of claim 1, wherein the urging step comprises urging the die block with a hydraulic ram.

7. The method of claim 1, further comprising the step of positioning a cover slip over the sample plate prior to the urging step.

8. The method of claim 1, wherein the urging step comprises urging the die block into contact with the sample plate.

9. The method of claim 1, wherein:
    the stationary phase is supported on a first side of the sample plate, and
    the urging step comprises urging the die block into the first side of the sample plate.

10. The method of claim 1, further comprising the step of advancing a fluid through a number of fluid channels defined in the die block.

* * * * *